(12) United States Patent
Bond et al.

(10) Patent No.: US 9,421,023 B2
(45) Date of Patent: Aug. 23, 2016

(54) ULTRASONIC TRANSDUCER WITH SHOCK PULSING MASSES

(71) Applicant: Cybersonics, Inc., Erie, PA (US)

(72) Inventors: Geoffrey Bond, Erie, PA (US); Jeffrey J. Vaitekunas, Erie, PA (US); Charles A. Baker, Erie, PA (US)

(73) Assignee: Cybersonics, Inc., Erie, PA (US)

( * ) Notice: Subject to any disclaimer, the term of this patent is extended or adjusted under 35 U.S.C. 154(b) by 625 days.

(21) Appl. No.: 13/915,861

(22) Filed: Jun. 12, 2013

(65) Prior Publication Data
US 2014/0371636 A1    Dec. 18, 2014

(51) Int. Cl.
*A61B 17/32* (2006.01)
*A61B 17/22* (2006.01)

(52) U.S. Cl.
CPC ........... *A61B 17/22012* (2013.01); *A61B 2017/22011* (2013.01); *A61B 2017/22014* (2013.01)

(58) Field of Classification Search
CPC ............... A61B 17/22004; A61B 17/22012; A61B 17/2202; A61B 17/320016; A61B 17/32002; A61B 17/320068; A61B 2017/22005; A61B 2017/22011; A61B 2017/22014; A61B 2017/22027; A61B 2017/320028; A61B 5/151; A61B 5/15117; A61B 5/15144; A61B 5/1519; A61B 5/15192; B06B 2201/76; A61F 9/00745; A61F 9/00763; A61C 3/03
USPC ............... 606/167–172, 127, 128; 604/22
See application file for complete search history.

(56) References Cited

U.S. PATENT DOCUMENTS

| | | | |
|---|---|---|---|
| 6,617,760 B1 | 9/2003 | Peterson et al. | 310/328 |
| 6,689,087 B2 | 2/2004 | Pal et al. | 604/22 |

(Continued)

FOREIGN PATENT DOCUMENTS

| | | |
|---|---|---|
| DE | 19510920 A1 | 9/1996 |
| RU | 2179919 C2 | 2/2002 |

OTHER PUBLICATIONS

Stewart Sherrit; et al., *Modeling of Horns for Sonic/Ultrasonic Applications*, 1999, 5 pages.

(Continued)

*Primary Examiner* — Melanie Tyson
*Assistant Examiner* — Majid Jamialahmadi
(74) *Attorney, Agent, or Firm* — Ulmer & Berne LLP

(57) ABSTRACT

What is presented is an ultrasonic waveguide for the transmission of ultrasonic vibrations that establishes a plurality of node and anti-node positions that are each along the ultrasonic waveguide's central axis. The ultrasonic waveguide comprises a waveguide tube, which has both a proximal end and a distal end; a waveguide fitting, which has both a threaded end and a impact surface; and a spring, shock-pulsing mass, and stop. Both the spring and shock-pulsing mass are each positioned on the waveguide tube. Whereas, the stop is positioned on the waveguide tube and it is adapted to non-fixedly engage the spring and shock-pulsing mass. The impact surface of the waveguide fitting is located at an anti-node position, which is along the central axis of the ultra-sonic waveguide when its installed within ultrasonic transducer while in operation.

16 Claims, 15 Drawing Sheets

(56) References Cited

U.S. PATENT DOCUMENTS

| | | | |
|---|---|---|---|
| 6,863,136 B2 | 3/2005 | Bar-Cohen et al. | 175/55 |
| 6,875,220 B2 | 4/2005 | Du et al. | 606/169 |
| 7,387,612 B2 * | 6/2008 | Pal | A61B 17/16 601/2 |
| 7,740,088 B1 | 6/2010 | Bar-Cohen et al. | 175/415 |
| 8,038,630 B2 | 10/2011 | Pal et al. | 601/2 |
| 2004/0127925 A1 * | 7/2004 | Du | A61B 17/22012 606/167 |
| 2005/0209620 A1 * | 9/2005 | Du | A61B 17/32053 606/167 |
| 2009/0143804 A1 | 6/2009 | Palmer et al. | |
| 2010/0274269 A1 | 10/2010 | Song et al. | 606/159 |

OTHER PUBLICATIONS

Yoseph Bar-Cohen; et al., *Ultrasonic/Sonic Driller/Corer (USDC) as a Sampler for Planetary Exploration*, 2001, 10 pages.

Xiaoqi Bao; et al., *Rock Sampling Using the Ultrasonic/Sonic Driller/Corer (USDC) for In-situ Planetary Exploration*, 2006, 49 pages.

Moon, Kihwan; International Preliminary Report on Patentability issued in International Application No. PCT/US2014/041889; dated Dec. 15, 2015; 5 pages.

\* cited by examiner

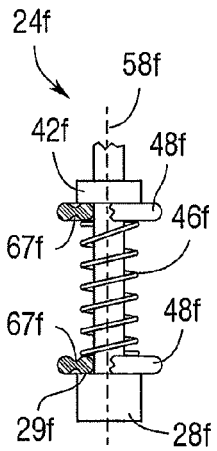 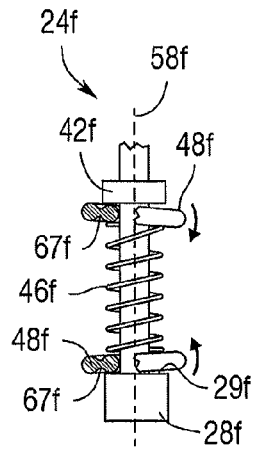 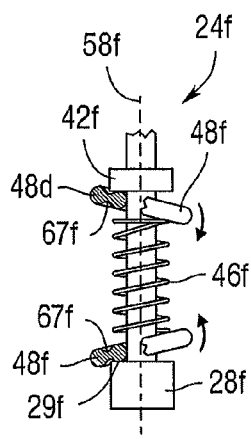 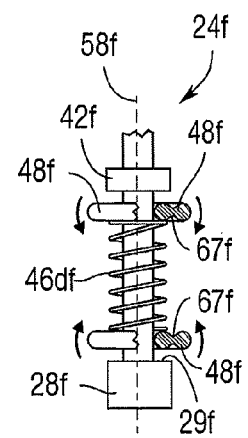
*Fig.16A*  *Fig.16B*  *Fig.16C*  *Fig.16D*
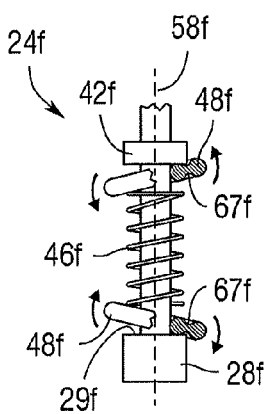 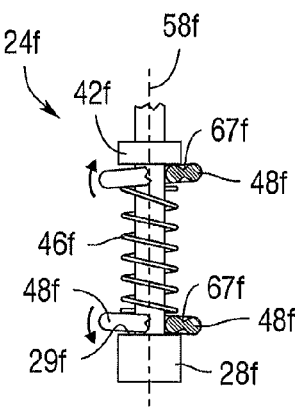 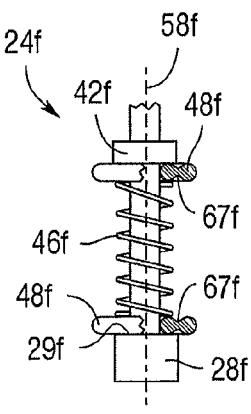
*Fig.16E*  *Fig.16F*  *Fig.16G*

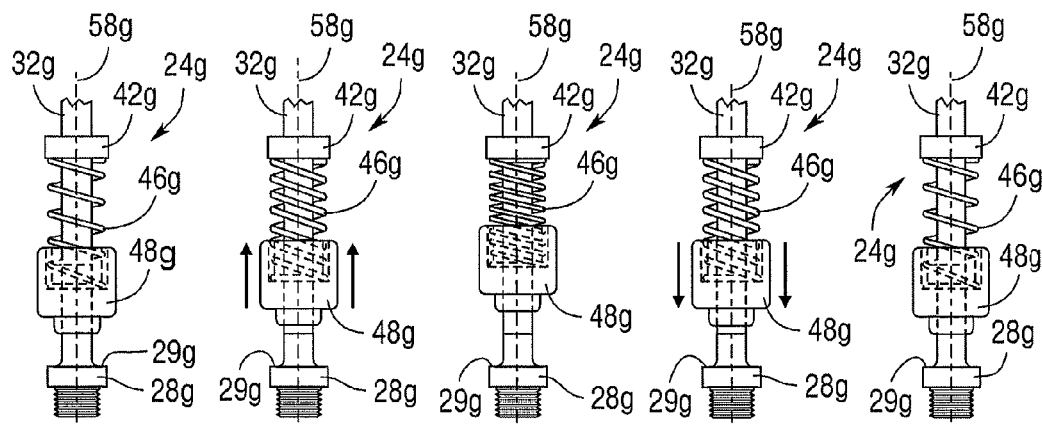
*Fig.20A*   *Fig.20B*   *Fig.20C*   *Fig.20D*   *Fig.20E*
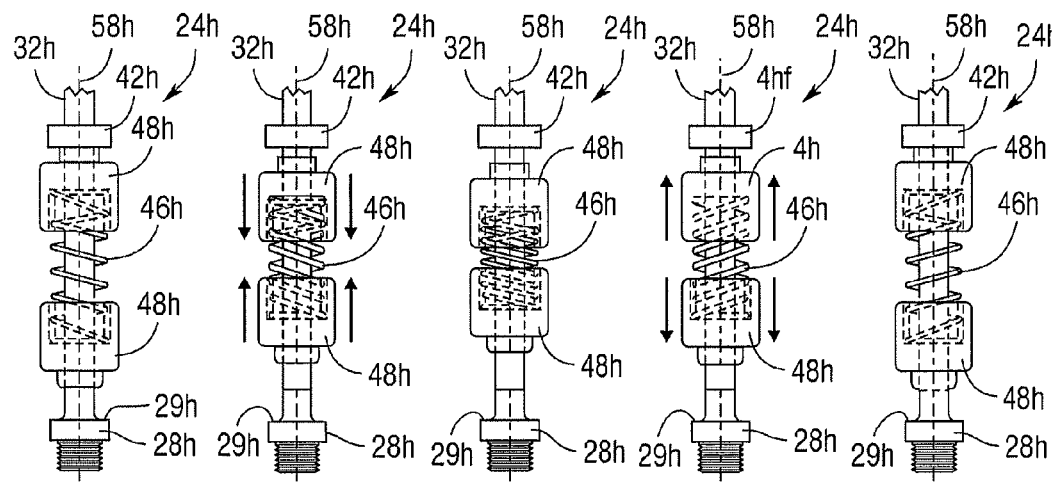
*Fig.21A*   *Fig.21B*   *Fig.21C*   *Fig.21D*   *Fig.21E*

ULTRASONIC TRANSDUCER WITH SHOCK PULSING MASSES

BACKGROUND

Ultrasonic transducers are used with percutaneous or transurethral surgical instruments that ablate blood clots, de-bulk calculi, drill/core bone, or the like. Ultra-sonic transducers operate in the range of 18 kilohertz and above. Research has determined that prior art ultrasonic transducers perform at less than optimal levels. Energy is lost as it travels down the ultrasonic waveguide component of these transducers affecting the performance efficiency of the transducers. Substandard performance creates a negative economic impact on sales of ultrasonic transducers because they do not stand up to the standards of users who expect certain levels of performance during surgical procedures. It has been found that the position of the stop on the ultrasonic waveguide greatly affects the performance of the ultrasonic transducer. Moreover, the shape, position, and movement of shock-pulsing masses also affect the performance of the ultrasonic transducer. What is presented are new arrangements of the ultrasonic waveguide and ultrasonic transducer as well as variations of shock-pulsing masses, each of which facilitate maximizing performance of the ultrasonic transducer.

SUMMARY

What is presented is a device for the transmission of ultrasonic vibrations, which establishes a plurality of node and anti-node positions along a central axis of an ultrasonic waveguide. The device comprises the ultrasonic waveguide. The ultrasonic waveguide comprises a waveguide tube, a waveguide fitting, and an impact surface. The waveguide tube has a proximal end and a distal end. The waveguide fitting has an attachment end and a waveguide tube coupler. The waveguide tube coupler is adapted to receive and fixedly secure to the proximal end of the waveguide tube. A stop is positioned on the ultrasonic waveguide and is adapted to non-fixedly engage the spring or shock-pulsing mass. A spring and a shock-pulsing mass are both also positioned on the ultrasonic waveguide, but they are interposed between the stop and the impact surface. Finally, the impact surface is positioned within at least one $\lambda/6$ of an anti-node position that occurs along the central axis of the ultra-sonic waveguide, when the attachment end of the waveguide fitting is attached to a device that is in operation.

The ultrasonic waveguide could have the stop on an anti-node position along the central axis of the ultrasonic waveguide. The ultrasonic waveguide could have the stop at a position that is within at least one $\lambda/6$, or even at least one $\lambda/3$ of an anti-node position along the central axis of the ultrasonic waveguide. The ultrasonic waveguide could have the spring, shock-pulsing mass, and stop each positioned on the waveguide fitting. Or the ultrasonic waveguide could have the spring, shock-pulsing mass, and stop each positioned on the waveguide tube.

The shock-pulsing mass could have a circular cross-section and a double dog bone shape around its central axis. Or the shock-pulsing mass could have a circular cross-section and a donut shape around its central axis. Or the shock-pulsing mass could have a circular cross-section and a tubular length, where the tubular length has a trench. The spring could abut against the stop. Or the spring could abut against the stop with the shock-pulsing mass abutting against the impact surface. The stop could also have a conical shape.

The ultrasonic waveguide could further comprise a second shock-pulsing mass, where the second shock-pulsing mass abuts against the stop, the shock-pulsing mass abuts against the impact surface, and the spring is positioned between the shock-pulsing mass and the second shock-pulsing mass. The ultrasonic waveguide could also further comprise a sealing implement, which is positioned on the ultrasonic waveguide. Where the stop and sealing implement each work in conjunction to create a seal when said ultrasonic waveguide is installed within an operating device.

BRIEF DESCRIPTION OF DRAWINGS

For a more complete understanding and appreciation of this invention, and its many advantages, reference will be made to the following detailed description taken in conjunction with the accompanying drawings.

FIG. 16A shows a side view of an embodiment of an ultrasonic waveguide in which two shock pulsing masses of FIG. 15A are at rest;

FIG. 16B shows a side view of an embodiment of an ultrasonic showing two shock-pulsing masses of FIG. 15A that have received an impact from an actuator vibration;

FIG. 16C shows a side view of an embodiment of an ultrasonic waveguide showing two shock pulsing masses of FIG. 15A in full wobble movement;

FIG. 16D shows a side view of an embodiment of an ultrasonic waveguide showing two shock pulsing masses of FIG. 15A at the pinnacle of their wobble movement;

FIG. 16E shows a side view of an embodiment of an ultrasonic waveguide showing two shock pulsing masses of FIG. 15A moving back to the rest position;

FIG. 16F shows a side view of an embodiment of an ultrasonic waveguide showing two shock pulsing masses of FIG. 15A immediately before returning to the rest position;

FIG. 16G shows a side view of an embodiment of an ultrasonic waveguide showing two shock pulsing masses of FIG. 15A after returning to rest;

FIG. 20A shows a side view of an embodiment of an ultrasonic waveguide with a shock pulsing mass as shown in FIGS. 19A through 19C at rest;

FIG. 20B shows a side view of an embodiment of an ultrasonic waveguide with a shock pulsing mass, as shown in FIGS. 19A through 19C, moving axially immediately after receiving an impact from actuator vibration;

FIG. 20C shows a side view of an embodiment of an ultrasonic waveguide with a shock pulsing mass, as shown in FIGS. 19A through 19C, at the pinnacle of its path of axial movement;

FIG. 20D shows a side view of an embodiment of an ultrasonic waveguide with a shock pulsing mass, as shown in FIGS. 19A through 19C, returning to the rest position;

FIG. 20E shows a side view of an embodiment of an ultrasonic waveguide with a shock pulsing mass, as shown in FIGS. 19A through 19C, after returning to rest;

FIG. 21A shows a side view of an embodiment of an ultrasonic waveguide with two shock pulsing masses, as shown in FIGS. 19A through 19C, at rest;

FIG. 21B shows a side view of an embodiment of an ultrasonic waveguide with two shock pulsing masses, as shown in FIGS. 19A through 19C, moving axially immediately after receiving an impact from actuator vibration;

FIG. 21C shows a side view of an embodiment of an ultrasonic waveguide with two shock pulsing masses, as shown in FIGS. 19A through 19C, at the pinnacle of their path of axial movement;

FIG. 21D shows a side view of an embodiment of an ultrasonic waveguide with two shock pulsing masses, as shown in FIGS. 19A through 19C, returning to the rest position;

FIG. 21E shows a side view of an embodiment of an ultrasonic waveguide with two shock pulsing masses, as shown in FIGS. 19A through 19C, after each has returned to rest;

DETAILED DESCRIPTION

Figure 1:
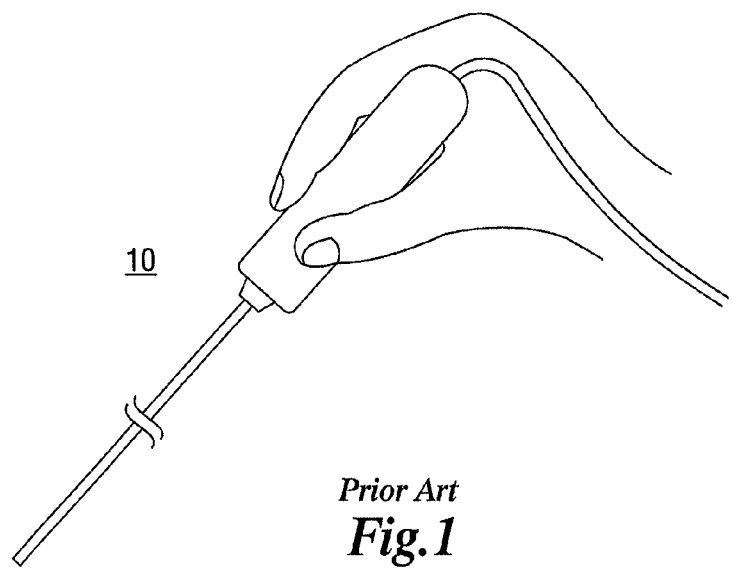
FIG. 1 shows a prior art ultrasonic transducer being used in a typical manner.

Referring to the drawings, some of the reference numerals are used to designate the same or corresponding parts through several of the embodiments and figures shown and described. Corresponding parts are denoted in different embodiments with the addition of lowercase letters. Variations of corresponding parts in form or function that are depicted in the figures are described. It will be understood that variations in the embodiments can generally be interchanged without deviating from the invention.

Figure 2:
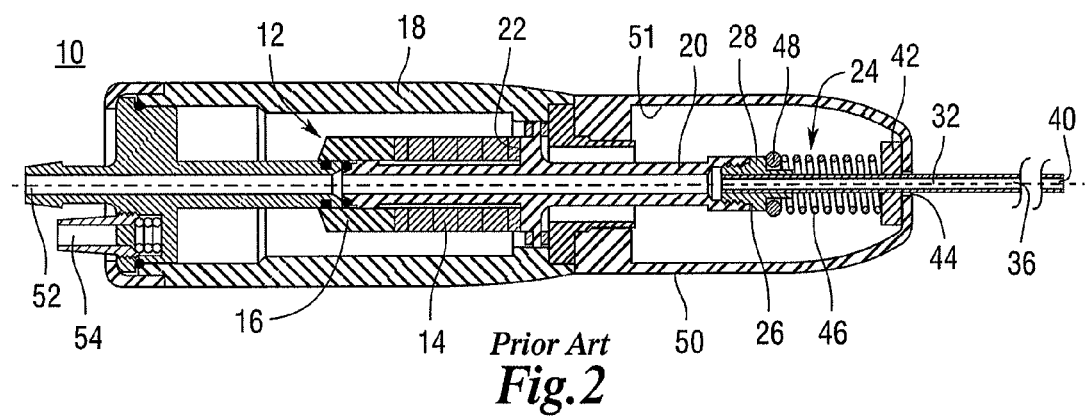
FIG. 2 shows a cross-section of a prior art ultrasonic transducer.
Figure 3:
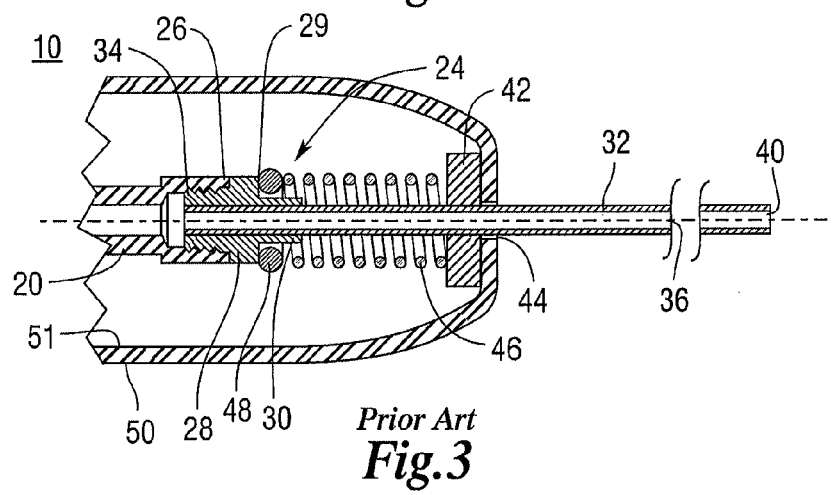
FIG. 3 shows a close up cross-section of the ultrasonic waveguide of the ultrasonic transducer of FIG. 2.

As shown in FIGS. 1 through 3, common prior art ultrasonic transducers 10 generally include an actuator 12 for generating transverse vibrations at ultrasonic frequencies. These frequencies are typically formed from a plurality of piezoelectric crystals 14 and a back plate 16. A power source (not shown) sends electricity to the piezoelectric crystals 14 causing them to vibrate longitudinally against the back plate 16, causing transverse vibrations to emanate through the horn 20 towards an ultrasonic waveguide 24. The ultrasonic waveguide 24 subsequently vibrates with the piezoelectric crystals 14. It will be understood that any element able to cause transverse vibrations from the ultrasonic transducer 10 through the ultrasonic waveguide 24, such as a magnetostrictive assembly, may work.

A housing 18 is provided to enclose the actuator 12. Typically, the housing 18 is made from some variety of plastic material because of its fluid-proof characteristics. However, it should be understood that the housing 18 may be made from any material that is fluid-proof; such as, but not limited to, metallic materials.

A hollow tubular horn 20 is joined to the actuator 12 through an abutment 22, at its proximal end, which facilitates amplification of the actuator 12 vibration. An ultrasonic waveguide 24 is secured to the horn 20 at its distal end 26 through a waveguide fitting 28. The attachment end 38 of the waveguide fitting 28 threadably secures the ultrasonic waveguide 26 to the horn 20. The waveguide fitting 28 has a waveguide tube coupler 30, with a impact surface 29, adapted to receive and fixedly secure to the proximal end 34 of a waveguide tube 32, sometimes called an elongated probe tube member, creating an attachment site, allowing for a lumen 36 within the waveguide tube 32 to pass through and connect with the hollow central portion of the horn 20. The distal end 40 of the waveguide tube 32 is the working end of the ultrasonic transducer 10, which comes into contact with blood clots, calculi, bone, etc. The ultrasonic waveguide 24 receives ultrasonic vibrations generated from the actuator 12 and transmits them through the waveguide tube 32 to engage and assist in ablating blood clots, break up calculi, drill bone, etc.

A stop 42, which is positioned on and joined to the waveguide tube 32, engages both a spring 46 and a shock-pulsing mass 48 that are both interposed between the stop 42 and the impact surface 29 of the waveguide fitting 28. The stop 42 adjoins a nosecone 50 that encloses the components of the ultrasonic waveguide 24, excluding the portion of the waveguide tube 32 extending through an opening 44 at the tip of the nosecone 50. The stop 42 is held in place against the inner surface 51 of the nosecone 50 in such a way that the stop 42 compresses the spring 46, which in turn provides resistance for the shock-pulsing mass 48 to vibrate against (as discussed below). The nosecone 50 is joined to the housing on the ultrasonic transducer 10.

The shock-pulsing mass 48 is positioned to oscillate, in response to ultrasonic vibrations, between the impact surface 29 of the waveguide fitting 28 and the spring 46. The spring 46 in turn provides a physical resistance that is created as the spring 46 pushes against the stop 42, which also in turn returns the shock-pulsing mass 48 to its original position of rest against the impact surface 29 of the waveguide fitting 28.

Each time the shock-pulsing mass 48 is returned to its position at rest, the shock-pulsing mass 48 impacts with the impact surface 29 of the waveguide fitting 28, generating a shock pulse (not shown) that travels longitudinally (axially) to the distal end 40 of the waveguide tube 32. It should be noted that the horn 20 also facilitates and induces these shock pulses. The transmission of these shock pulses facilitate forces of jack-hammer like axial movement (discussed in more detail below) at the distal end 40 of the waveguide tube 32, which can be effective in ablating blood clots, breaking large stones into small pieces, drilling hard object, etc., through the use of the ultrasonic transducer 10. The finer particles created during this use are aspirated through the lumen 40 of the waveguide tube 32 and then through the horn 20, which communicates with a suction port 52 interconnected with a vacuum source (not shown).

It should be noted that ultrasonic transducers 10 are typically powered by an external power source (not shown) through a power source conduit 54 protruding from the housing 18. However, it should also be understood that the ultrasonic transducer 10 may be powered by an internal power source (not shown), such as, a battery operation source or the like.

Efficiency loss has been an issue with prior art ultrasonic transducers 10. Energy transfer from the actuator 12 through the waveguide tube 32 is not maximized and energy loss occurs between both ends of the ultrasonic waveguide 24. This energy loss creates issues for the user when implementing the ultrasonic transducer 10 during surgical procedures because the performance of the ultrasonic transducer 10 is not working to the standards of these procedures. Ultimately, performance issues create a negative economic impact on sales of ultrasonic transducers 10 since potential users purchase competing instruments that are perceived to perform closer to the standard of their surgical needs.

Figure 4:
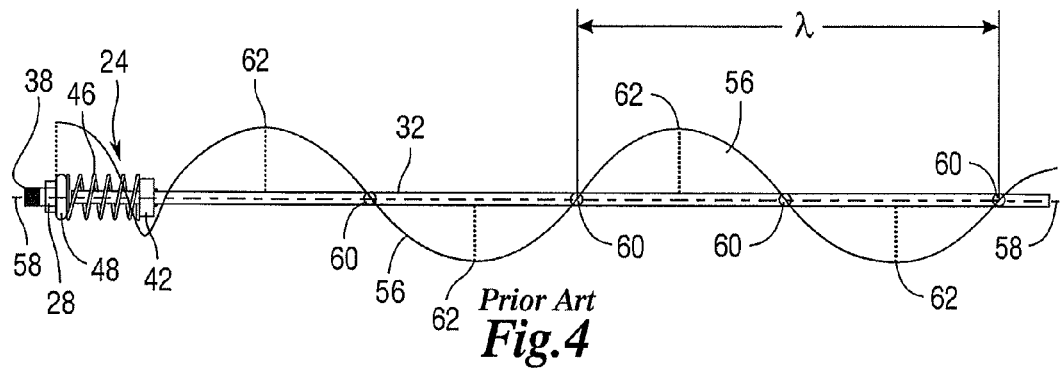
FIG. 4 shows a prior art configuration of an ultrasonic waveguide superimposed on a graphical representation of a wavelength representing the axial displacement along the waveguide tube.

As can be seen in FIG. 4, ultrasonic vibrations transmitted lengthwise along the ultrasonic waveguide 24 create a series of reverberation positions and stagnation positions. These reverberation positions and stagnation positions create a sinusoidal-like wave 56 that is collinear with the a central axis 58, running lengthwise along the ultrasonic waveguide 24. Each time the wave 56 crosses the plane of the central axis 58 a node 60 position is created (high stress), which represents stagnations where the waveguide tube 32 does not move axially. Each time the wave 56 reaches a position at its peak amplitude an anti-node 62 position is created (low stress), located directly below the corresponding peak amplitude, which represents reverberations where axial displacements of the waveguide tube 32 peaks and most axial movement occur. Each full wavelength of the wave 56 is represented by $\lambda$, which both starts at and ends at a node 60 position. Due to the physics behind the wave, the impact surface 29 of the ultrasonic transducer fitting 28 is the first established anti-node 62 position of the plurality of node 60 positions and anti-node 62 positions, along the central axis 58 of the ultra-sonic waveguide 24.

One having ordinary skill in the art will find that the half wave length of a fixed free bar, can be determined using equations and systems that are well known in the art. While in ordinary use of the ultrasonic transducer 10, at 21 kHz and a tube diameter of 3.76 mm, the first node 60 position along the waveguide tube 32 occurs at approximately 1.5 inches from the impact surface 29 of the waveguide fitting 28. The first anti-node 62 position occurs at approximately 3.6 inches from the impact surface 29 of the waveguide fitting 28 and every 4.5 inches thereafter along the waveguide tube 32. It will be understood, depending on the frequency of ultrasonic vibrations emanating from the actuator, or frequency of shock-pulses, these node 60 positions and anti-node 62 positions may occur at different positions along the central axis 58 of the ultrasonic waveguide 24.

Shock-pulsing masses 48 create a "jack hammering" effect to improve the effectiveness of the ultrasonic transducer 10 by creating shock pulses. The function of the shock pulses can be described mathematically. The axial displacement of the distal end 40 of the horn 20 is described by the equation below:

$$x = -\frac{A}{\omega}\cos\omega t$$

where x is the tip displacement of distal end 40 of the horn 20, $A/\omega$ is the amplitude of displacement, t is time, and $\omega$ is the angular frequency, $2\pi f$ where f is the frequency.

The displacement velocity of the distal end 40 of the horn 20 during vibrations is found by taking the time derivative of the axial displacement and described by the equation below:

$$v = A\sin(\omega t)$$

where v is the displacement velocity. When the energy loss and time duration of the impact is negligible and the mass of the horn 20 is much larger than the shock-pulsing mass 48, using the conservation of momentum and energy, the interaction between the horn 20 and shock-pulsing mass 48 is described by the equation below:

$$v_{mf} = v_{mi} + 2v$$

where $v_{mi}$ is the shock-pulsing mass 48 velocity prior to interaction with the horn 20 and $v_{mf}$ is the shock-pulsing mass 48 velocity after interaction with the horn 20.

The spring constant of a spring changes by the length of the spring, the number of turns, and diameter of the wire used to construct the spring. By changing these variables in the spring 46, the spring constant will increase or decrease the characteristics of the spring 46. The shock-pulsing mass 48 and the stop 42 can also be manipulated, to strengthen or weaken the impact energy of each shock pulse traveling down the central axis 58 of the ultrasonic waveguide 24. Impact energy manipulation can be effective with different applications of the ultrasonic transducer 10, e.g., at ablating blood clots vs. drilling through bone. In particular, the more mass a shock-pulsing mass 48 has, the more impact energy there will be each time an impact occurs between the stop 42 and shock pulsing mass 48. In essence, adding mass to a shock-pulsing mass 48 facilitates axial displacement amplification at the distal end 40 of the waveguide tube 32. There is, however, a limit to which having too much mass will impede the functions of the ultrasonic waveguide 24.

Figure 5:
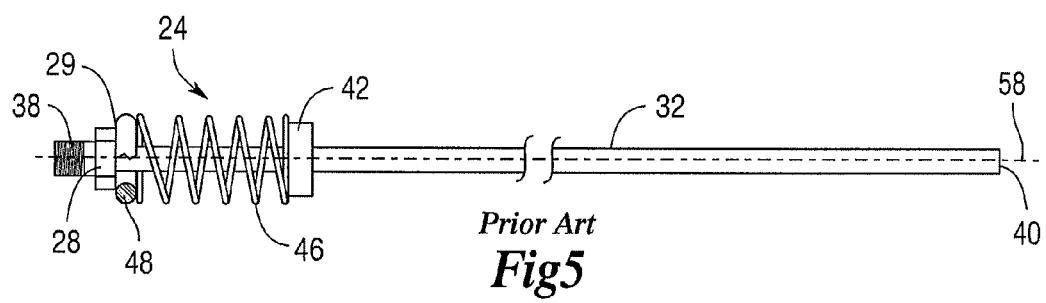
FIG. 5 shows a side view of a prior art ultrasonic waveguide.
Figure 6A:
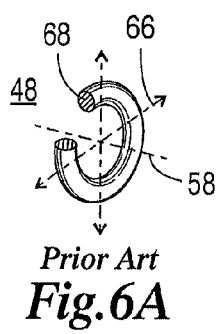
FIG. 6A shows a perspective view of a prior art shock pulsing mass with a circular cross-section and a donut shape around its central axis.
Figure 6B:
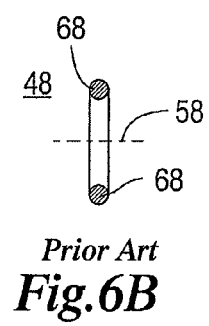
FIG. 6B shows a cross-section of the shock pulsing mass of FIG. 6A.

As can be seen in FIGS. 5, 6A and 6B, prior art ultrasonic waveguides 24 use a shock-pulsing mass 48 that has a circular cross-section 66 and donut shape 68 around the central axis 58. The problem with the shape and design of these shock-pulsing masses 48 is that these masses are greatly limited geometrically. When the height of the shock-pulsing mass 48 is modified, the mass takes on an ovular shape that drastically restricts its freedom of movement while oscillating. When the diameter of the circular cross-section 66 is modified, the shock-pulsing mass 48 quickly becomes disproportionately too heavy and is too restricted for proper freedom of movement. The flat sides of the shock-pulsing mass 48 also cause a loss of impact energy through transverse forces during each impact between the stop 42 and shock-pulsing mass 48, particularly when the corner of the stop 42 or waveguide fitting 28 impacts with the shock pulsing mass 48. Due to these transverse forces, it is difficult to direct the energy of each impact directly forward so as to transfer the energy down the ultrasonic waveguide 24. Too much of the impact energy is misdirected and lost. So, the goal of maximizing energy per impact being transmitted to the distal end 40 of the waveguide tube 32 cannot be achieved with the prior art shape of the shock-pulsing mass 48. Another problem associated with this shock-pulsing mass 48 shape and design is that the shock-pulsing masses 48 will ruin the edges of the impact surface 29 on the horn 20 by striking these edges like a hammer until they have deformed. This deformation not only causes the shock-pulsing mass 48 to function incorrectly, it also makes it difficult to grip the horn 20 when removing the horn 20 by twisting it off with a wrench.

Figure 7:
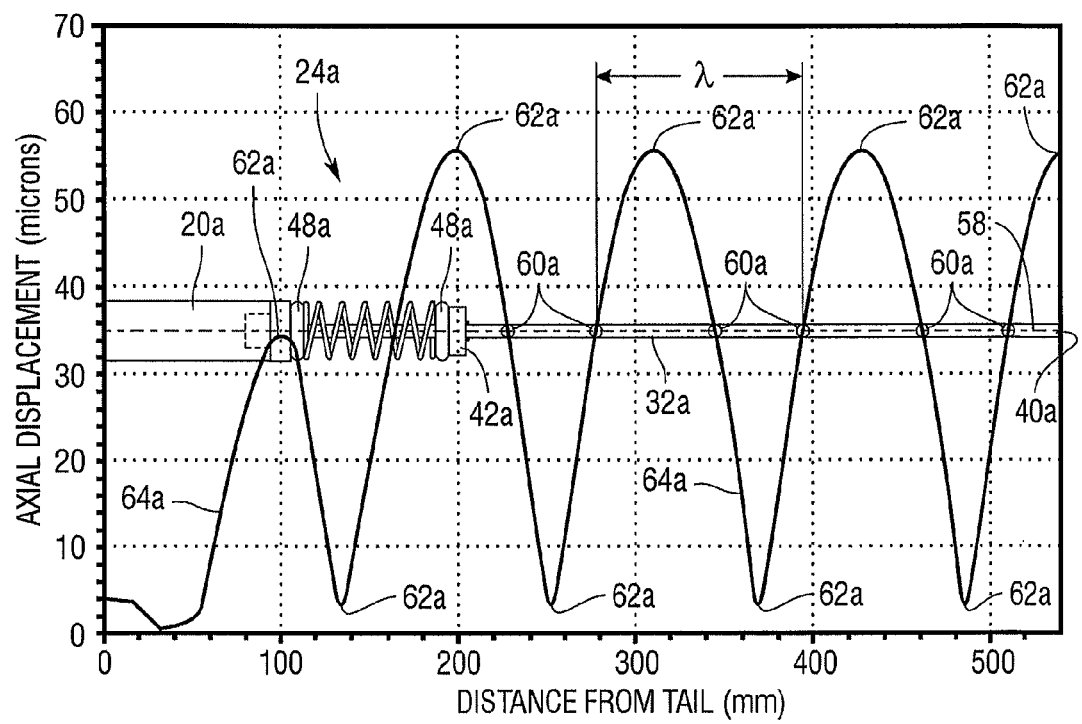
FIG. 7 shows the new configuration of the ultrasonic waveguide, which facilitates maximum performance of the ultrasonic transducer, superimposed on a graph showing a wavelength representing the axial displacement along the waveguide tube.

With all of the limitations of the prior art ultrasonic transducers 10, there is much room for improvement. A variety of improvements are presented and discussed herein. As can be seen in FIG. 7, one of the ways to maximize the performance of ultrasonic transducers is to manipulate the location of various components to take advantage of the vibrations of the ultrasonic waveguide 24a. The solid line wave 64a represents displacement of the waveguide tube 32a in the axial direction (i.e. horizontally along the x-axis). Each full wavelength of the solid line wave 64a is represented by $\lambda$, which both starts at and ends at a node 60a position. The first peak of axial displacement represents the first anti-node 62a position, which in this embodiment is at the impact surface 29a. This anti-node 62a position has less axial displacement than the rest of the anti-node 62a positions due to the resonant gain along the probe (i.e., the amplitude of axial displacement, represented by the anti-node 62a positions, is higher on the waveguide tube 32a).

By arranging the impact surface 29a to be directly at this first anti-node 62a position, displacement occurring at the distal end of waveguide tube 32a is improved. Positioning the impact surface 29a at an anti-node position 62a, causes a corresponding anti-node position 62a to occur at the distal end 40a of the waveguide tube 32a. It has also been found that the closer the stop 42a is positioned to an anti-node 62a position, the more axial displacement will occur at the distal end of the waveguide tube 32a. A minimal amount of additional axial displacement will begin to occur at distal end 40a of the waveguide tube 32a when the stop is positioned at least $\lambda/3$ from an anti-node 62a position, with more axial displacement occurring the closer the stop 42a is to the anti-node 62a position. For an effective amount of axial displacement at the distal end of the waveguide tube 32a, the stop 42a should be positioned on the waveguide tube 32a within at least $\lambda/6$ from an anti-node 62a position that occurs along the central axis 58a of the ultrasonic waveguide 24a. To ensure maximum effectiveness with this configuration, the stop 42a should be positioned as exactly as possible at the anti-node 56a position. However, as explained above, one having ordinary skill in the art will understand that the benefits of this ultrasonic waveguide 24a configuration will also be seen when the stop 42a is near the anti-node 62a position.

As can be seen in FIG. 7, there are approximately 20 millimeters on each side of each anti-node 62a position before reaching the closest node 60a position. The performance enhancing effects of this arrangement decrease every millimeter that the stop 42a is positioned off to the side of one of the anti-node 62a positions. Thus, if the stop 42a is positioned more than approximately 10 millimeters on either side of the anti-node 62a position, most of the enhancing effects of this ultrasonic waveguide 24a configuration will be lost.

Figure 8:
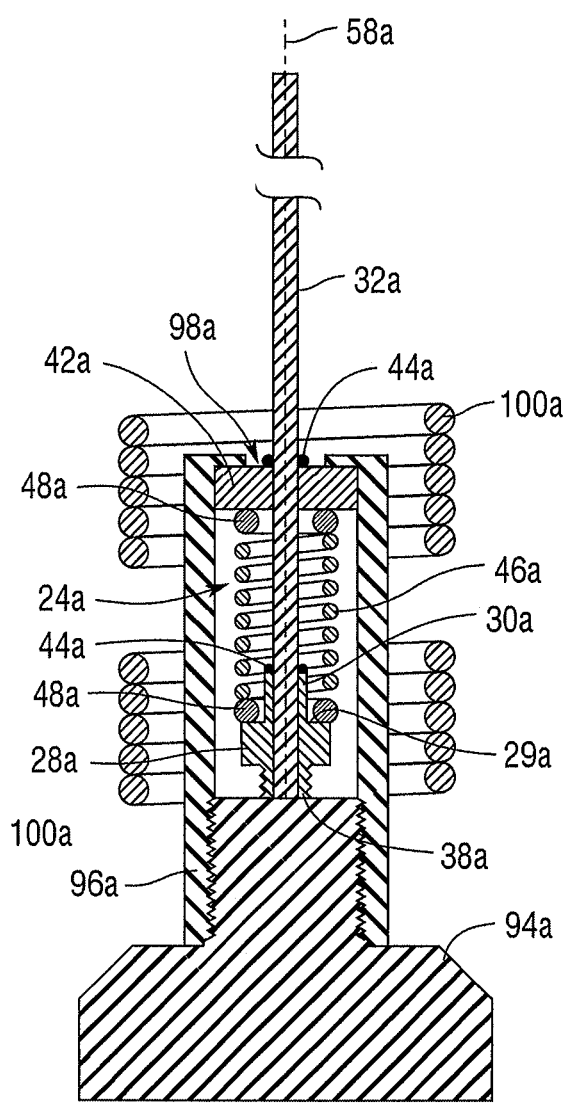
FIG. 8 shows a cross-section of the components used in the manufacturing process creating an ultrasonic waveguide.

Ultrasonic waveguides 24a that incorporate this concept are created through a unique manufacturing process. As shown in FIG. 8, the ultrasonic waveguide 24a, is assembled on a brazing base 94a at its respective position. The brazing base 94a provides a stable base for each of the components used in the manufacture of the ultrasonic waveguide 24a. The brazing base 94a is typically made from ceramic material able to withstand the heat used in the manufacturing process. However, it will be understood that any material able to withstand the heat used in the manufacturing process will suffice.

First, the attachment end 38 of a waveguide fitting 28a is placed on the brazing base 94a. A waveguide tube 32a is then inserted into the waveguide tube coupler 30a of the waveguide fitting 28a, creating an attachment site. Brazing compound 44a is added to the attachment site. In the embodiment shown in this figure, two shock-pulsing masses 48a and a spring 46a are each slid over the waveguide tube 32a to rest against the waveguide fitting 28a. The shock-pulsing mass 48a shown in this figure has a circular cross-section around the central axis or a circular cross-section and tubular length. However, it will be appreciated that the shock-pulsing mass could have any shape so long as the shock-pulsing mass functions properly. The number and location of the masses can vary as discussed herein or otherwise.

A stop 42a is then inserted over the waveguide tube 32a to rest against the other components. The stop 42a is the uppermost component on the waveguide fitting 24a while mounted on the brazing base 94a. In the example shown here, the stop 42a abuts against one of the two shock pulsing masses 48a but (as discussed in greater detail herein) it will be appreciated that the stop 42a could abut against the spring 46a. It will also be appreciated that the ultrasonic waveguide 24 could be manufactured to incorporate only one shock-pulsing mass 48a.

After the components of the ultrasonic waveguide 24a are assembled, a compression sleeve 96a is inserted around and slid over the waveguide tube 32a through a sleeve opening 98 on the compression sleeve 96a. The compression sleeve 96a is threadably mounted to its respective position on the brazing base 94a. When properly mounted, the compression sleeve 96 will bias against the stop 42a and hold the spring 46a in a constant state of compression in such a way that the stop 42a is situated at an anti-node position along the central axis 58 of the ultrasonic waveguide 24a. A second layer of brazing compound 44a is then placed on the intersection of the stop 42a and waveguide tube 32a, through the sleeve opening 98a of the compression sleeve 96a.

A pair of induction heating coils 100a is then positioned around the compression sleeve 96a and the ultrasonic waveguide 24a, near each position where brazing compound 44a has been placed. The induction coils 100a are then activated, heating the brazing compound 44a and causing it to permanently join both of the positions where it has been applied on the ultrasonic waveguide 24a.

As discussed earlier, maximum performance of axial displacement at the distal end 40 of the waveguide tube 32a occurs when the stop 42a is at an anti-node position. However, one having ordinary skill in the art still sees performance benefits when the stop 42a is not exactly on, but near the anti-node position. Therefore, in some instances, performance may be maximized when the stop 42a is near the anti-node position.

Figure 9A:
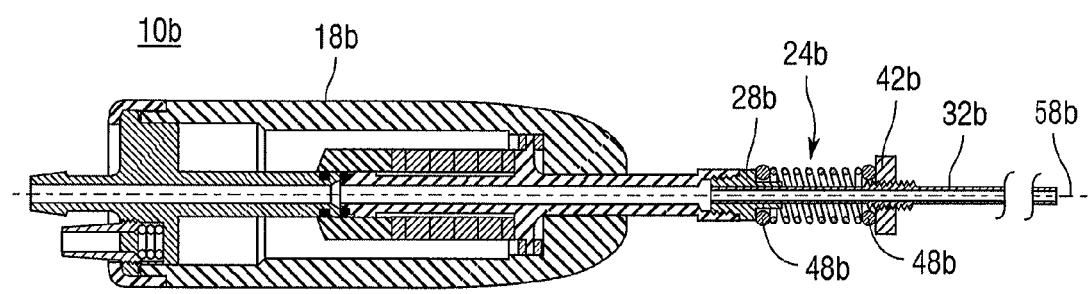
FIG. 9A shows a cross-section of an embodiment of an ultrasonic transducer having a stop with an adjustable position along the central axis of the ultrasonic waveguide.
Figure 9B:
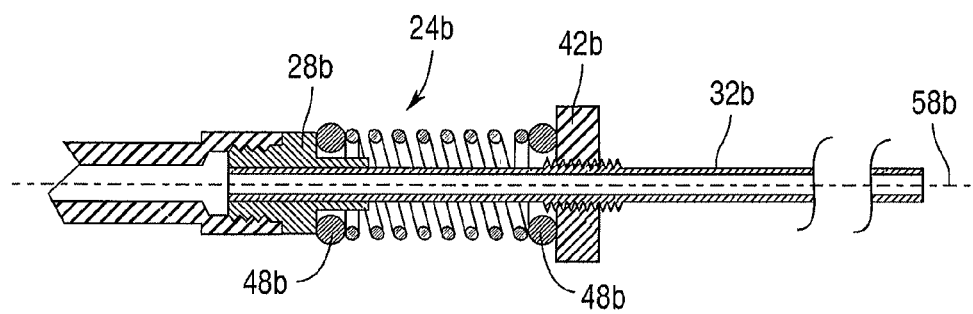
FIG. 9B shows a close up cross-section of the ultrasonic waveguide of the ultrasonic transducer of FIG. 9A.

FIGS. 9A and 9B show an embodiment in which performance is maximized by making the position of the stop 42b on the ultrasonic waveguide 24b to be adjustable. The ultrasonic transducer 10b incorporates a stop 42b with an adjustable position. The stop 42b is threadably secured to the waveguide tube 32b allowing for it to have an adjustable position. This embodiment of ultrasonic waveguide 24b has two shock-pulsing masses 48b. One of two shock-pulsing masses 48b is pressed up against the stop 42b by a spring 46b. Due to the pushing force of the spring 46b, the position of the shock-pulsing mass 48b will also adjust with the stop 42b. This adjustment also changes the compression characteristics of the spring 46b, which will coincidentally affect the movement characteristics of each shock-pulsing mass 48b positioned on the ultrasonic waveguide 24b. It should be noted that this embodiment of the ultrasonic transducer 10b, the housing 18b does not have a nosecone joined to it, but a nosecone could be added to cover the ultrasonic waveguide 24b of the ultrasonic transducer 10b.

Figure 10A:
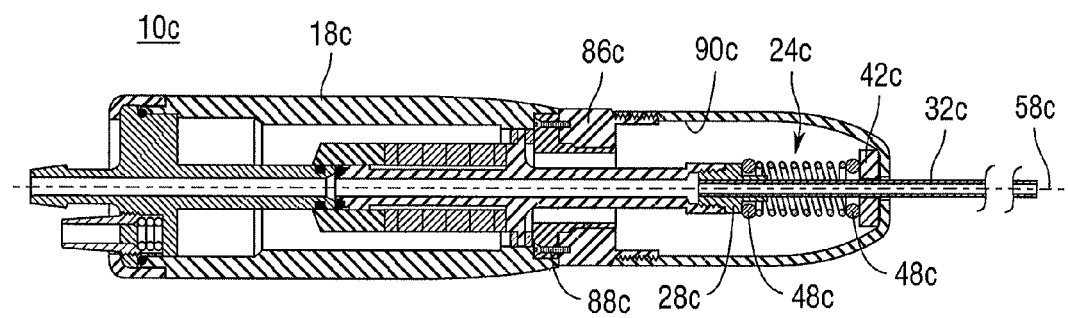
FIG. 10A shows a cross-section of another embodiment of an ultrasonic transducer having a stop with an adjustable position along the central axis of the ultrasonic waveguide.
Figure 10B:
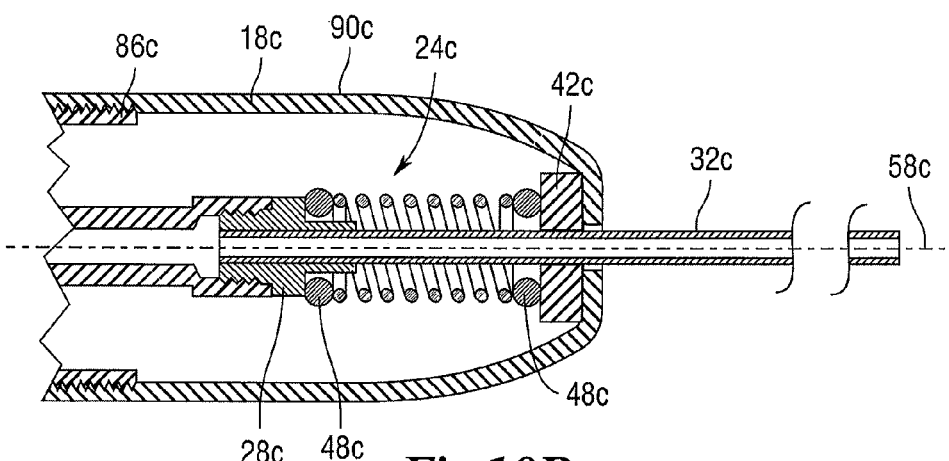
FIG. 10B shows a close up cross-section of the ultrasonic waveguide of FIG. 10A.

FIGS. 10A and 10B show another embodiment in which performance is maximized by making the position of the stop 42c to be adjustable on the ultrasonic waveguide 24c. In this embodiment, the housing 18c of the ultrasonic transducer 10c joins to an inner nosecone 86c at a joining site 88c. A portion of the inner nosecone 86c is threaded so that the inner nosecone 86c can adjustably secure to corresponding threading on an outer nosecone 90c. Attaching the outer nosecone 90c to the inner nosecone 86c through threading allows for the outer nosecone 90c to have an adjustable position along the central axis 58c of the ultrasonic transducer 10c, when the outer nosecone 90c is twisted.

A stop 42c that is non-fixedly joined to the waveguide tube 32c allowing for it to have an adjustable position by sliding along the length of the waveguide tube 32c. The stop 42c abuts and is pressed against the outer nosecone 90c, through the pushing force of a spring 46c, so that when the position of the outer nosecone 90c is adjusted, the stop 42c will adjust correspondingly with the position of the outer nosecone 90c. The ultrasonic waveguide 24c has two shock-pulsing masses 48c on it. One of two shock-pulsing masses 48c is pressed up against the stop 42c by the spring 46c and the position of the shock-pulsing mass 48c will also adjust with the outer nosecone 90c and stop 42c. This adjustment also changes the compression characteristics of the spring 46c, which will coincidentally affect the movement characteristics of each shock-pulsing mass 48c positioned on the ultrasonic waveguide 24c.

Figure 11:
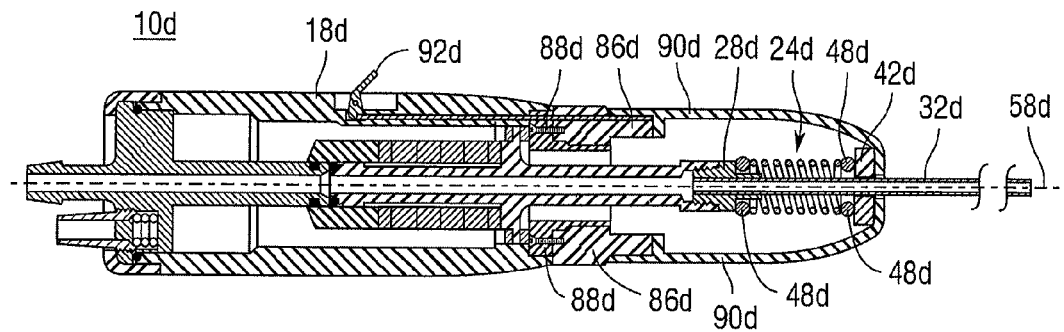
FIG. 11 shows a cross-section of another embodiment of an ultrasonic transducer having a stop with an adjustable position along the length of the ultrasonic waveguide.

Another embodiment of the ultrasonic transducer 10d incorporating a stop 42d with an adjustable position is shown in FIG. 11. In this embodiment, the housing 18d of the ultrasonic transducer 10d joins to an inner nosecone 86d at a joining site 88d. A portion of the inner nosecone 86d is adjustably secured to an outer nosecone 90d. The outer nosecone 86d is controlled by an adjusting device 92d, which in this embodiment is a lever. The outer nosecone 90d is adjusted by setting the adjustment device 92d to push and pull the outer nosecone 90d as required. It should be understood that the adjusting device 92d may be something other than a lever. Other embodiments of the adjusting device include, but are not limited to, push buttons, slides, twisting apparatus, lock and key apparatuses, etc.

The stop 42d is joined to the outer nosecone 90d. So that when the position of the outer nosecone 90d is adjusted, the stop 42d will adjust correspondingly with the position of the outer nosecone 90d.

The ultrasonic waveguide 24d has has two shock-pulsing masses 48d. One of two shock-pulsing masses 48d is pressed up against the stop 42d by a spring 46d. Due to the pushing force of the spring 46d, the position of the shock-pulsing mass 48d will also adjust with the outer nosecone 90d and stop 42d. This adjustment also changes the compression characteristics of the spring 46d, which will coincidentally affect the movement characteristics of each shock-pulsing mass 48d positioned on the ultrasonic waveguide 24d. It will be understood that the number of configuration of shock-pulsing masses can vary depending on the application.

Figure 12A:
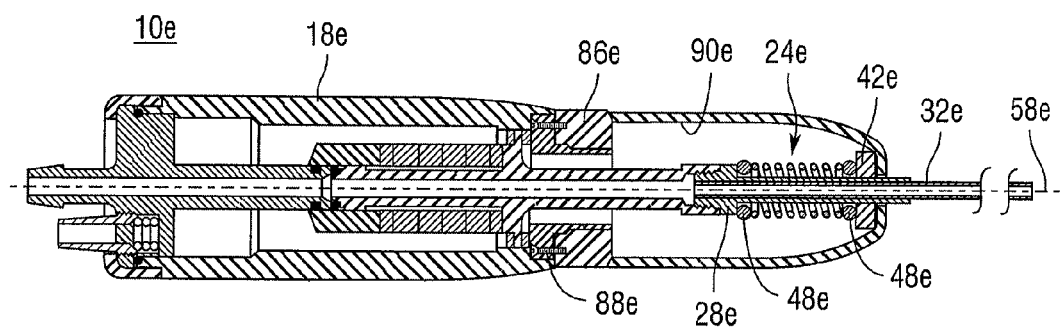
FIG. 12A shows a cross-section of an embodiment of an ultrasonic transducer having an ultrasonic waveguide with an elongated waveguide fitting.
Figure 12B:
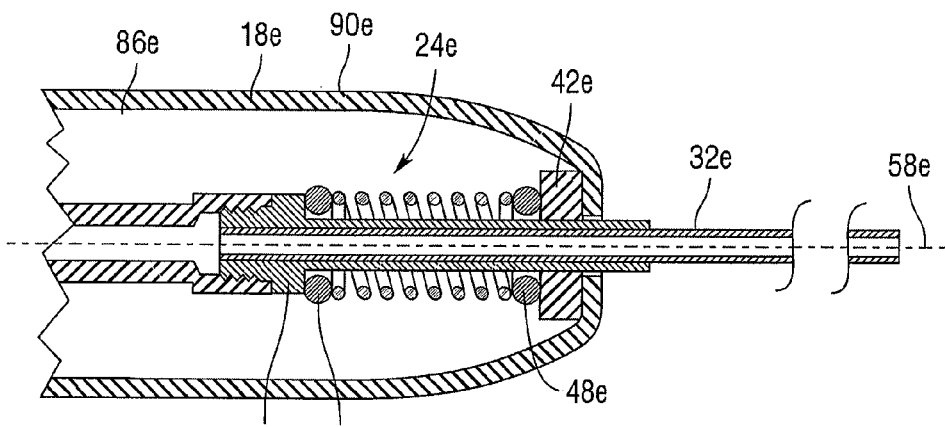
FIG. 12B shows a close up cross-section of the ultrasonic waveguide of the ultrasonic transducer of FIG. 12A.

It has also been found that variations on the orientation of the components of the ultrasonic waveguide 24 can produce the advantage discussed above. As shown in FIGS. 12A and 12B, the spring 46e, shock-pulsing masses 48e, and stop 42e are positioned on the waveguide fitting 28e while still producing the same maximum displacement at the distal end 40e of the waveguide tube 32e as previous embodiments. In this embodiment, the waveguide fitting 28e is elongated to the point that is protrudes through the opening 44e at the tip of the nosecone 50e. The stop 42e, which is positioned on and joined to the waveguide fitting 28e, engages both the spring 46e and the shock-pulsing mass 48e that are both interposed between the stop 42e and the impact surface 29e of the waveguide fitting 28e. The stop 42e adjoins the nosecone 50e that encloses the components of the ultrasonic waveguide 24e, excluding the portions of the waveguide fitting 28e and waveguide tube 32e extending through the opening 44e at the tip of the nosecone 50e. The stop 42e is held in place against the inner surface 51e of the nosecone 50e in such a way that the stop 42e compresses the spring 46e, which in turn provides resistance for the shock-pulsing mass 48e to vibrate against (as discussed above). The nosecone 50e is joined to the housing on the ultrasonic transducer 10e.

The attachment end 38e of the waveguide fitting 28e threadably secures the ultrasonic waveguide 26e to the horn 20e. The waveguide fitting 28e has a waveguide tube coupler 30e, with a impact surface 29e that is adapted to receive and fixedly secure to the proximal end 34e of a waveguide tube 32e, creating an attachment site. In this embodiment, the attachment site begins at a position external to the nosecone 50e and runs through the body of the waveguide fitting 28e to the horn 20e. Similar to the embodiments above, the ultrasonic waveguide 24e receives ultrasonic vibrations generated from the actuator 12e and transmits them through the waveguide tube 32e to engage and assist in ablating blood clots, break up calculi, drill bone, etc.

As previously discussed, another area where performance can be improved is with the shock-pulsing mass. As can be seen in FIGS. 13 through 15B, to overcome the performance limitations associated with prior art shapes, changes to the shape of the shock-pulsing mass 48f have been made. As best seen in FIGS. 15A and 15B, a double dog bone shape is created by increases the diameter of the cross-section 66f of the shock-pulsing mass 48f and subsequently carving a circular shaped divot 67f from the center of the cross-section 66f on each side of the shock-pulsing mass 48f. The double dog bone shape 68f adds more material to the shock-pulsing mass 48f without restricting its freedom of movement, and avoids disproportionately increasing the diameter of the circular cross-section 66f or modifying the height of the shock-pulsing mass 48f.

Figure 13:
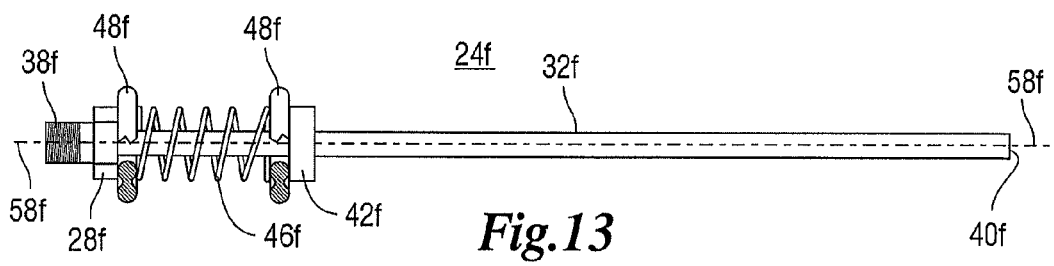
FIG. 13 shows a side view of an ultrasonic waveguide having two shock-pulsing masses with circular cross-sections and a double dog bone shape around their central axis.
Figure 14:
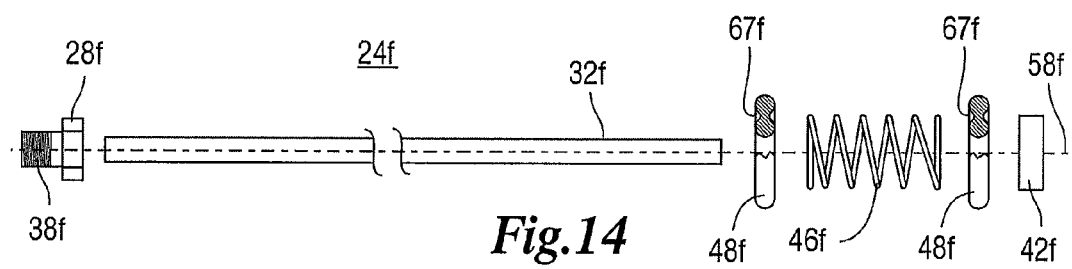
FIG. 14 shows an exploded view of FIG. 12.
Figure 15A:
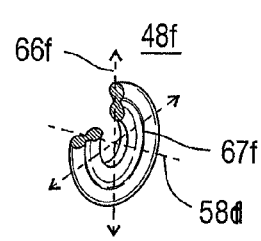
FIG. 15A shows a perspective view of a shock pulsing mass with a circular cross-section and a double dog bone shape around its central axis.
Figure 15B:
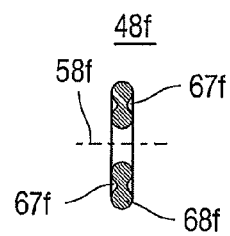
FIG. 15B shows a cross-section of the shock pulsing mass of FIG. 15A.
Figure 17:
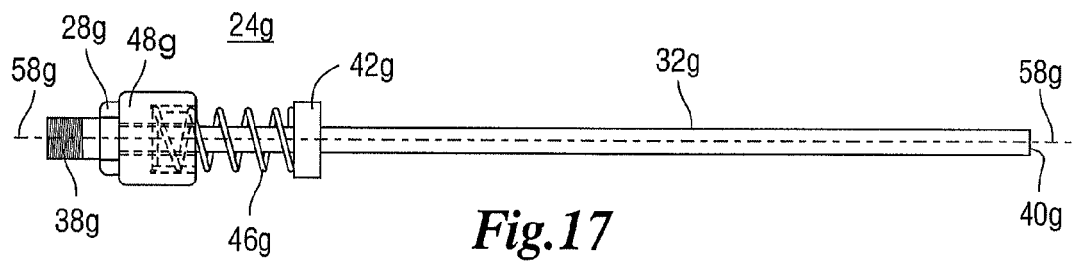
FIG. 17 shows a side view of another embodiment of an ultrasonic waveguide having an axial moving shock-pulsing mass with circular cross-sections and tubular length.
Figure 18:
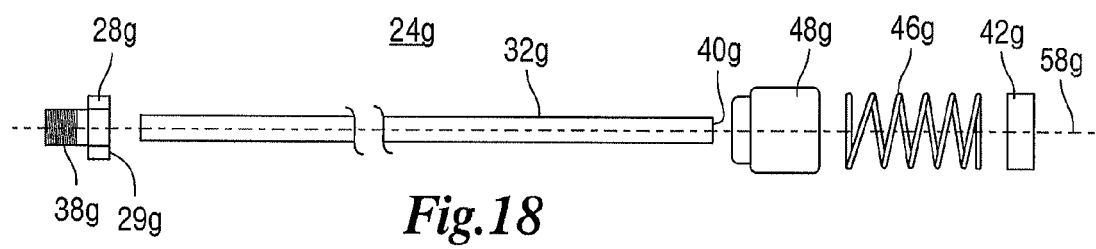
FIG. 18 shows an exploded view of the ultrasonic waveguide of FIG. 17.
Figure 19A:
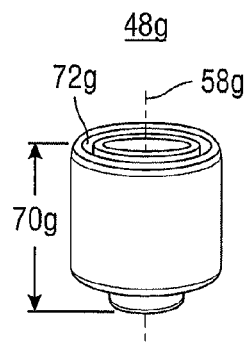
FIG. 19A shows a perspective view of the embodiment of the shock pulsing mass of FIGS. 17 and 18.
Figure 19B:
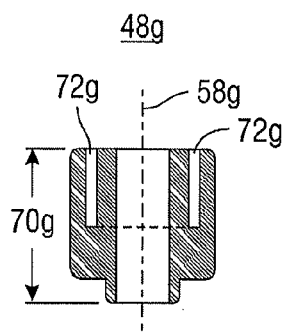
FIG. 19B shows a cross-section of the shock pulsing mass of FIGS. 17 and 18.
Figure 19C:
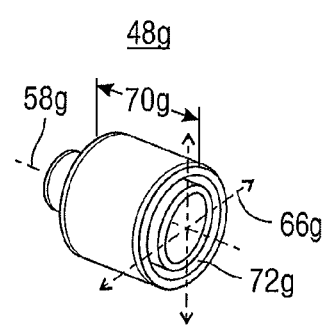
FIG. 19C shows a perspective view of the shock pulsing mass of FIGS. 17 and 18.

FIGS. 13 and 14 show an embodiment of the ultrasonic waveguide 24f that comprises two shock-pulsing masses 48f, each having a circular cross-section 66f and a double dog bone shape 68f around the central axis 58f. It will be appreciated that it is necessary for only one side of the shock-pulsing mass 48f to have a circular shaped divot 67f carved out of its cross-section, so long as the side with the divot directly impacts with the stop 42f or waveguide fitting 28f.

The performance of the double dogbone shape 68f shock pulsing mass 48f is illustrated in FIGS. 16A through 16G, which shows a close up of the ultrasonic waveguide 24f of FIGS. 13 and 14 in operation. When the ultrasonic transducer 10f is in operation, both shock-pulsing masses 48f wobble as they oscillate in response to the ultrasonic vibrations. The shock pulsing masses 48f are able to move up and down concentric to the central axis 58f of the ultrasonic waveguide 24f as well as freely without restriction in transverse directions. This freedom of movement allows for uneven impacts of the shock-pulsing masses 48f with the stop 42f or waveguide fitting 28f where only a portion of side of the shock-pulsing mass 42f makes contact, during each impact. To achieve maximum performance of the ultra-sonic waveguide 24f, a shock-pulsing mass 48f should be disposed between the spring 46f and impact surface 29f of the waveguide fitting 28f and another shock-pulsing mass 48f disposed between the spring 46f and stop 42f.

As best shown in FIGS. 16C and 16E, each time a portion of the shock-pulsing mass 48f impacts the corner of the stop 42f or waveguide fitting 28f, the circular divot 67f catches with the corner of that element during each impact. The circular divot 67f reduces transverse impacts and maximizes surface contact, ensuring an optimal amount of impact energy is forced forward and along the ultrasonic waveguide 24f. As the side portion of the shock-pulsing mass 48f impacts with the corner of the stop 42f it also causes lower frequency shock pulses to travel both longitudinally and transversely along the central axis 58f of the ultrasonic waveguide 24f. These lower frequency shock pulses subsequently cause a low frequency "wagging" displacement at the distal end 40f of the waveguide tube 32f. "Wagging" is when displacement of the distal end 40f of the waveguide tube 32f occurs simultaneously in both the longitudinal and transverse directions, which can be very beneficial for certain applications of the ultrasonic transducer 10f.

The shock-pulsing mass 48f is typically made from surgical steel or stainless steel. The energy of impacts from each of the shock-pulsing masses 48f can be adjusted by using different types of material. Shock-pulsing masses 48f made from a material softer than steel tend to have an elastic impact, causing each impact to absorb more energy so that the shock-pulsing mass 48f moves slower and is less effective. If the material is too soft, too much energy will be absorbed, causing axial displacement at the distal end 40f of the waveguide tube 32f to be so weak that the shock-pulsing masses 48f are ineffective. Shock-pulsing masses 48f made from a material more rigid than steel, have faster oscillation movement and absorb less energy after colliding with the stop 42f or waveguide fitting 28f. If the material is too ridged, the shock-pulsing masses 48f will be prone to cracking and fracturing after long term use. It will be understood that the energy of impacts from the shock-pulsing masses 48f can also be adjusted by changing the characteristics of the spring 46f, such as, but not limited to, the spring constant or its compression.

FIGS. 17 through 21E show a different embodiment of shock-pulsing mass 48g in which the mass and weight of the shock-pulsing mass 48g is increased at the cost of its freedom of movement. Since restriction of movement in this instance is not a concern, mass and weight can be added directly to the circular cross-section of the shock-pulsing mass 48g to help boost the energy of each impact. As can be seen in FIGS. 17 through 19C, an embodiment of the ultrasonic waveguide 26g comprises a shock-pulsing mass 48g having a circular cross-section 66g and a tubular length 70g around the central axis 58g. A trench 72g, carved from the tubular length 70g, allows for more mass to be added without interfering with the functionality of the spring 46g.

The trench 72g is approximately half way into the tubular length 70g of the shock-pulsing mass 48g and is wide enough to accommodate the spring 46g into the trench 72g when installed on the ultrasonic waveguide 26g. This ensures that the shock-pulsing mass 48g remains stable and completely concentric to the central axis 58g when oscillating. In this embodiment, the shock-pulsing mass 48g is disposed between the spring 46g and impact surface 29g of the waveguide fitting 28g. However, it will be appreciated that the shock-pulsing mass 40g could be situated between the stop 42g and spring 46g.

As can be seen in FIGS. 20A through 20E, the restricted axial movement of the shock-pulsing mass 48g creates high energy axial impacts, having very little energy loss due to transverse movement when the shock-pulsing mass 48g impacts with the stop 42g. Here, the entire surface of the shock-pulsing mass 48g impacts the waveguide fitting 28g all at once, causing axially moving shock pulses with a lot of energy to travel along the ultrasonic waveguide 24g. The distal end of the waveguide tube 32g will in turn have maximum displacement axially in a longitudinal jack-hammering like movement.

As discussed above, shock-pulsing mass 48g is typically made from surgical steel or stainless steel. The energy of impacts from the shock-pulsing mass 48g can be adjusted by using different types of material. Shock-pulsing masses 48g made from a material softer than steel tend to have an elastic impact, causing each impact to absorb more energy so that the shock-pulsing mass 48g moves slower and is less effective. If the material is too soft, too much energy will be absorbed, causing axial displacement at the distal end 40g of the waveguide tube 32g to be so weak that the shock-pulsing masses 48g are ineffective. Shock-pulsing masses 48g made from a material more rigid than steel will have faster oscillation movement and absorb less energy after colliding with the stop 42g or another shock-pulsing mass 48g. However if the material is too ridged the shock-pulsing mass 48g will be prone to cracking and fracturing after long term use. It will be understood that the energy of impacts from the shock-pulsing mass 48g can also be adjusted by changing the characteristics of the spring 46g, such as, but not limited to, the spring constant or its compression.

As can be seen in FIGS. 21A through 21E, in another embodiment of the ultrasonic waveguide 24h, two shock-pulsing masses 48h can be installed on the ultrasonic waveguide 24h. One shock-pulsing mass 48h is disposed between the spring 46h and the impact surface 29h of the waveguide fitting 28h, while the other is disposed between the stop 42h and the spring 46h. This restricted transverse movement of the shock-pulsing masses 48h creates high energy transverse impacts, with very little energy loss as the shock-pulsing masses 48h impact with either the stop 42h or waveguide fitting 28h. Here, the entire surface of each shock-pulsing masses 48h impacts either the waveguide fitting 28h or stop 42h at once. The distal end 40h of the waveguide tube 32h will in turn be caused to have maximum displacement axially in a jack-hammering like movement.

Having more than one shock-pulsing mass 48h on the ultrasonic waveguide 24h facilitates shock pulse amplification by reinforcing each pulse with additional impact energy. One having ordinary skill in the art will see that the position and effect of the second shock-pulsing mass 82h will manipulate the shock pulses such that they may effectively change the axial displacement at the distal end of the ultrasonic waveguide 24h, which can be useful for different applications of the ultrasonic transducer.

Figure 22:
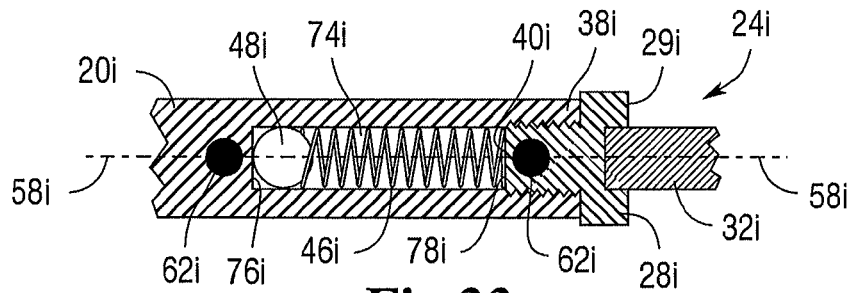
FIG. 22 shows a cross-section of the horn and ultrasonic waveguide on another embodiment of the ultrasonic transducer.

Other embodiments of shock-pulsing masses are also possible in which the shock-pulsing masses are not located on the ultrasonic waveguide 24i, but behind the waveguide fitting 28i. As shown in FIG. 22, shock pulses disrupting the ultrasonic vibrations wavelengths can be created by engaging the shock-pulsing mass 48i within a centrally located cavity 74i within the horn 20i. In this embodiment, the shock-pulsing 48i mass in effect impacts directly with the proximal end 76i of the cavity, facilitating axial displacement at the distal end 40i of the ultrasonic waveguide 24i. In this embodiment, the proximal end of the ultrasonic waveguide 26i is the tip of the attachment end 38i of the waveguide fitting 28i. The horn 20i is joined to the actuator (not shown) of the ultrasonic transducer (not shown). The distal end of the horn 20i threadably secures to the proximal end 78i of the ultrasonic waveguide 24i. Two anti-node 62i positions are located at the proximal end 78i of the ultrasonic waveguide 24i and at the proximal end 76i of the cavity 74i.

The distal end of the cavity 74i coincides with the distal end of the horn 20i. The inner walls around the distal end of the cavity 74i are threaded, which allows the proximal end 78i of the ultrasonic waveguide 24i to threadably secure to the horn 20i and the distal end of the cavity. The cavity 74i is typically created by burrowing directly into the horn 20i through the central axis 58i for a preferred distance and subsequently carving out threads at its distal end. It should also be understood that in embodiments where the horn incorporates a centrally located cavity no lumen exists within the waveguide tube 32i and the horn 20i is not hollow.

A shock-pulsing mass 48i, which in this embodiment is a spherically shaped ball, such as a ball bearing, and a spring 46i are each engaged within the cavity 74i. Here, at rest, the shock-pulsing mass 48i is pressed against the proximal end 76i of the cavity 74i by the force of the spring 46i. Axial displacement from the anti-node 62i position at the proximal end 76i of the cavity 74i impacts with the shock-pulsing mass 48i and thrusts it forward. The spring 46i provides resistance and pushes back on the shock pulsing mass 48i, returning the shock-pulsing mass 48i and impacting against the proximal end 76i of the cavity 74i, providing jackhammer-like pulses along the ultrasonic waveguide 24i. This motion occurs very rapidly and cyclically, causing the shock-pulsing mass 48i to oscillate, and the shock-pulses to form a corresponding wave as they travel along the ultrasonic waveguide 24i in series. It should be appreciated that the shock-pulsing mass 48i could have a shape other than spherical, so long as the shock-pulsing mass 48i can create shock-pulses while enclosed within the cavity 74i. Such shapes include, but are not limited to, a piston shape, an octagonal shape, or a cube shape, etc.

Figure 23:
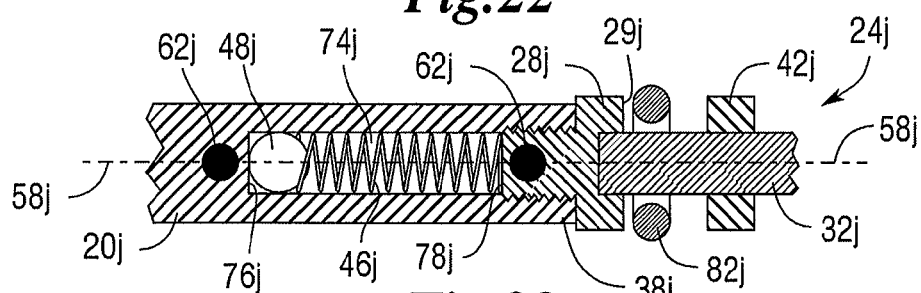
FIG. 23 shows a cross-section of the horn and ultrasonic waveguide on another embodiment of the ultrasonic transducer.

As shown in FIG. 23, in another embodiment of the ultrasonic transducer in which the horn 20j has a shock-pulsing mass 48j engaged within a centrally located cavity 74j, a second shock-pulsing mass 82j is positioned on the ultrasonic waveguide 24j. In this embodiment, the shock-pulsing mass 48j is spherically shaped, such as a ball bearing, whereas, the second shock-pulsing mass 82j has a circular cross-section and donut shape around the central axis 58j. It should be appreciated that the shock-pulsing mass 48j could have a shape other than spherical, so long as the shock-pulsing mass 48j can create shock-pulses while enclosed within the cavity 74j. Such shapes include, but are not limited to, a piston shape, an octagonal shape, or a cube shape, etc.

Here, the second shock-pulsing mass 82j is non-fixedly engaged on the body of the ultrasonic waveguide 24j, in between the waveguide fitting 28j and stop 42k. The shock pulses emanating forward from the proximal end 78*j* of ultrasonic waveguide 24*j* will cause the second shock-pulsing mass 82*j* to thrust forward with each shock pulse. This thrusting movement helps to amplify the shock pulse by reinforcing it with additional impact energy from the second shock-pulsing mass 82*j* impacting the stop 42*j*. One having ordinary skill in the art will see that the position and effect of a the second shock-pulsing mass 82*j* will manipulate the shock pulses such that they may effectively change the axial displacement at the distal end of the ultrasonic waveguide 82*j*, which can be useful for different applications of the ultrasonic transducer.

Figure 24:
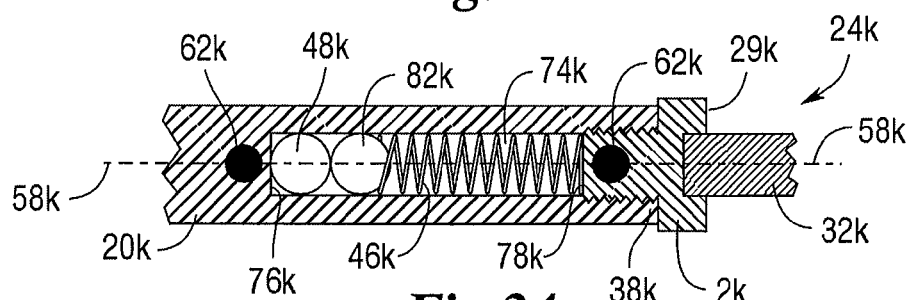
FIG. 24 shows a cross-section of the horn and ultrasonic waveguide on another embodiment of the ultrasonic transducer.

As shown in FIG. 24, in another embodiment of the ultrasonic transducer two shock-pulsing masses 48*k* are engaged within the centrally located cavity 74*k*. Here, the shock-pulsing mass 48*k* and second shock-pulsing mass 82*k* are each a spherically shaped ball bearing. At rest, the shock-pulsing mass 48*k* is pressed against the proximal end 76*k* of the cavity 74*k* and the second shock-pulsing mass 82*k* is pressed against the shock-pulsing mass 48*k* on its opposite side, both being pressed by the force of the spring 46*k*. Axial displacement from the anti-node 62*k* position at the proximal end 76*k* of the cavity 74*k* impacts with the shock-pulsing mass 48*k*, which in turn impacts with the second shock-pulsing mass 82*k* and each are thrust forward. The spring 46*k* provides resistance and pushes back on both the shock pulsing mass 48*k* and second shock pulsing mass 82*k*, returning each mass and impacting the proximal end 76*k* of the cavity 74*k* providing jackhammer-like pulses along the ultrasonic waveguide 24*k*. This motion occurs very rapidly and cyclically, causing the shock-pulsing mass 48*k* and second shock-pulsing mass 82*k* to oscillate, and the shock-pulses to form a corresponding wave as they travel along the ultrasonic waveguide 24*k* in series. It should be appreciated that the shock-pulsing mass 48*k* and second shock pulsing mass 82*k* could each have a shape other than spherical, so long as the shock-pulsing mass 48*k* and second shock pulsing mass 82*k* can create shock-pulses while enclosed within the cavity 74*k*. Such shapes include, but are in no way limited to, a piston shape, an octagonal shape, or a cube shape, etc.

The second shock-pulsing mass 82*k* helps to amplify each shock pulse by reinforcing it with additional impact energy from the second shock-pulsing mass 82*k* impacting the proximal end 78*k* of the ultrasonic waveguide 24*k*. One having ordinary skill in the art will see that the position and effect of a the second shock-pulsing mass 82*k* will manipulate the shock pulses such that they may effectively change the axial displacement at the distal end of the ultrasonic waveguide 24*k*, which can be useful for different applications of the ultrasonic transducer.

Figure 25:
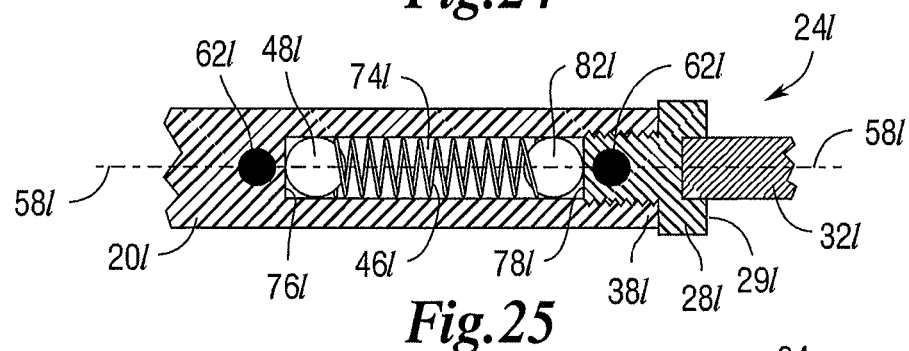
FIG. 25 shows a cross-section of the horn and ultrasonic waveguide on another embodiment of the ultrasonic transducer.

As shown in FIG. 25, in another embodiment of the ultrasonic transducer a second shock-pulsing mass 82*l* is engaged within the centrally located cavity 74*l*. Here, the shock-pulsing mass 48*l* and second shock-pulsing mass 82*l* are each a spherically shaped ball bearings. At rest, the shock-pulsing mass 48*l* is pressed against the proximal end 76*l* of the cavity 74*l* and the second shock-pulsing mass 82*l* is pressed against the proximal end of the ultrasonic waveguide 78*l*, both being pressed by the forces of the spring 46*l*. Axial displacement from the anti-node 62*l* position at the proximal end 76*l* of the cavity 74*l* impacts with the shock-pulsing mass 48*l* and thrusts it forward. The spring 46*l* provides resistance and pushes back on both the shock pulsing mass 48*l* and second shock pulsing mass 82*l*, returning each and impacting the surface of their original positions. These impacts on the proximal end of the ultrasonic waveguide 78*l* provide jackhammer-like pulses along the ultrasonic waveguide 24*l*. This motion occurs very rapidly and cyclically, causing the shock-pulsing mass 48*l* to oscillate, and the shock-pulses to form a corresponding wave as they travel along the ultrasonic waveguide 24*l* in series. It should be appreciated that the shock-pulsing mass 48*l* and second shock pulsing mass 82*l* could each have a shape other than spherical, so long as the shock-pulsing mass 48*l* and second shock pulsing mass 82*l* can create shock-pulses while enclosed within the cavity 74*l*. Such shapes include, but are in no way limited to, a piston shape, an octagonal shape, or a cube shape, etc.

The second shock-pulsing mass 82*l* helps to amplify each shock pulse by reinforcing it with additional impact energy from the second shock-pulsing mass 82*l* impacting the proximal end 78*l* of the ultrasonic waveguide 24*l*. One having ordinary skill in the art will see that the position and effect of a the second shock-pulsing mass 82*l* will manipulate the shock pulses such that they may effectively change the axial displacement at the distal end of the ultrasonic waveguide 24*l*, which can be useful for different applications of the ultrasonic transducer.

Figure 26:
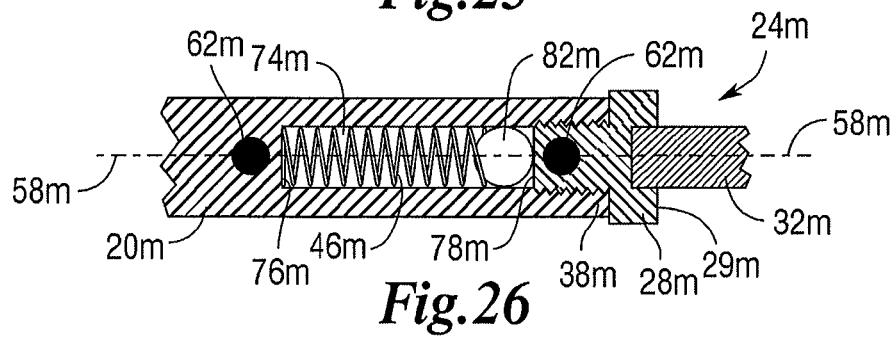
FIG. 26 shows a cross-section of the horn and ultrasonic waveguide on another embodiment of the ultrasonic transducer.

As shown in FIG. 26, in another embodiment of the ultrasonic transducer, a spherically shaped ball bearing shock-pulsing mass 48*m* is pressed against the proximal end 76*m* of the ultrasonic waveguide 78*m* by the force of the spring 46*m*. Axial displacement at the distal end of the cavity 74*m*, from the anti-node 62*m* position, impacts with the shock-pulsing mass 48*m*. The shock-pulsing mass 48*m* is pushed into the spring 46*m* where the spring 46*m* returns the shock-pulsing mass 48*m* and impacts the proximal end 78*m* of the ultrasonic waveguide 24*m*, providing jackhammer-like pulses along the ultrasonic waveguide 24*m*. This motion occurs very rapidly and cyclically, causing the shock-pulsing mass 48*m* to oscillate and the shock-pulses to form a corresponding wave as they travel along the ultrasonic waveguide 24*m* in series. It should be appreciated that the shock-pulsing mass 48*m* could have a shape other than a spherical, so long as the shock-pulsing mass 48*m* can create shock-pulses while enclosed within the cavity 74*m*. Such shapes include, but are in no way limited to, a piston shape, an octagonal shape, or a cube shape, etc.

Figure 27:
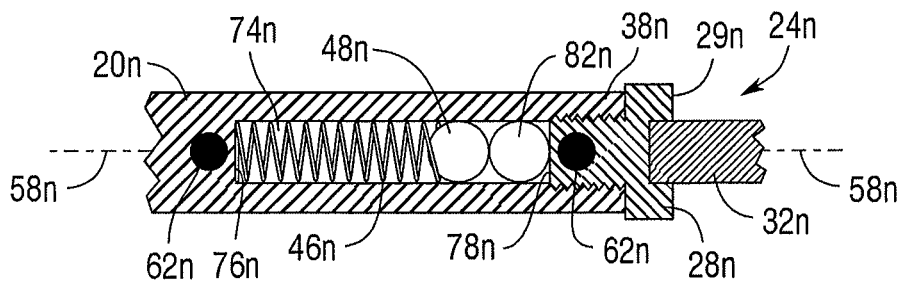
FIG. 27 shows a cross-section of the horn and ultrasonic waveguide on another embodiment of the ultrasonic transducer.

As shown in FIG. 27, in another embodiment of the ultrasonic transducer a second shock-pulsing mass 48*n* is engaged within the centrally located cavity 74*n*. Here, the shock-pulsing mass 48*n* and second shock-pulsing mass 82*n* are each a spherically shaped ball bearings. At rest, the shock-pulsing mass 48*n* and the second shock-pulsing mass 82*n* are both pressed against the proximal end 76*n* of the ultrasonic waveguide 24*n* by the force of the spring 46*n*. Axial displacement at the proximal end of the waveguide fitting 78*n*, from the anti-node 62*n* position, impacts with the second shock-pulsing mass 82*n*. Energy from the impact is subsequently pushed proximally through the shock-pulsing mass 48*n*, and each are thrust proximally. The spring 46*n* provides resistance and pushes back on both the shock pulsing mass 48*n* and second shock pulsing mass 82*n*, returning each and impacting the proximal end 78*n* of the waveguide fitting 28*n*, providing jackhammer-like pulses along the ultrasonic waveguide 24*n*. This motion occurs very rapidly and cyclically, causing the shock-pulsing mass 48*n* and second shock-pulsing mass 82*n* to oscillate, and the shock-pulses to form a corresponding wave as they travel along the ultrasonic waveguide 24*n* in series. It should be appreciated that the shock-pulsing mass 48*n* and second shock pulsing mass 82*n* could each have a shape other than a spherical, so long as the shock-pulsing mass 48*n* and second shock pulsing mass 82*n* can create shock-pulses while enclosed within the cavity 74*n*. Such shapes include, but are in no way limited to, a piston shape, an octagonal shape, or a cube shape, etc.

The second shock-pulsing mass 82*n* helps to amplify each shock pulse by reinforcing it with additional impact energy from the second shock-pulsing mass 82*n* impacting the proximal end 78*n* of the ultrasonic waveguide 24*n*. One having ordinary skill in the art will see that the position and effect of a the second shock-pulsing mass 82*n* will manipulate the shock pulses such that they may effectively change the axial displacement at the distal end of the ultrasonic waveguide 24*n*, which can be useful for different applications of the ultrasonic transducer.

Figure 28:
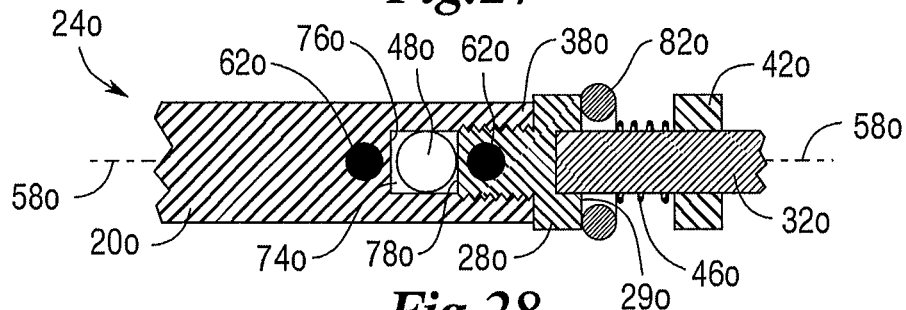
FIG. 28 shows a cross-section of the horn and ultrasonic waveguide on another embodiment of the ultrasonic transducer.

As shown in FIG. 28, in another embodiment of the ultrasonic transducer in which the horn 20*o* has a shock-pulsing mass 48*o* engaged within a centrally located cavity 74*o*, a second shock-pulsing mass 82*o* is positioned on the ultrasonic waveguide 24*o*. In this embodiment, the shock-pulsing mass 48*o* is a spherically shaped ball bearing, whereas, the second shock-pulsing mass 82*o* has a circular cross-section and donut shape around the central axis 58*o*. It should be appreciated that the shock-pulsing mass 48*o* could have a shape other than spherical, so long as the shock-pulsing mass 48*o* can create shock-pulses while enclosed within the cavity 74*o*. Such shapes include, but are in no way limited to, a piston shape, an octagonal shape, or a cube shape, etc.

Here, the cavity 74*o* is calibrated to allow the shock-pulsing mass 48*o* to oscillate freely without the need of a spring pushing the mass against either the proximal end 76*o* of the cavity 74*o* or the proximal end 78*o* of the ultrasonic waveguide 24*o*. Axial displacement at the proximal end 76*o* of the cavity 74*o*, from the anti-node 62*o* position, impacts with the shock-pulsing mass 48*o*. The shock-pulsing mass 48*o* is then thrust forward, impacting with the proximal end 78*o* of the ultrasonic waveguide 24*o*. Axial displacement at the proximal end 78*o* of the ultrasonic waveguide 24*o*, from a second anti-node 62*o* position at the proximal end 78*o* of the ultrasonic waveguide 24*o*, will subsequently impact the shock-pulsing mass and cause it to ricochet back towards the proximal end 76*o* of the cavity 74*o*. These corresponding axial displacements create the shock-pulsing mass to move in a back and forth movement 48*o* between the proximal ends of both the cavity 74*o* and the ultrasonic waveguide 24*o*, creating a corresponding shock pulse along the ultrasonic waveguide 24*o*. One having ordinary skill in the art will see the length of the cavity 74*o* must be properly calibrated or the shock-pulsing mass 48*o* will not to move back and forth when the ultrasonic transducer (not shown) is held horizontally to the ground. One having ordinary skill in the art will also see that the frequency of ultrasonic vibrations will have to be modified so that the anti-node 62*o* positions will be located at their positions as shown.

The second shock-pulsing mass 82*o* is non-fixedly engaged on the body of the ultrasonic waveguide 24*o*, in between the waveguide fitting 28*o*, spring 46*o*, and stop 42*o*. At rest, the second shock-pulsing mass 82*o* is pressed against the waveguide fitting 28*o* of the ultrasonic waveguide 24*o* by the force of the spring 46*o*. Ultrasonic energy emanating forward from the proximal end 78*o* of ultrasonic waveguide 24*o* will cause the second shock-pulsing mass 82*o* to thrust forward. The spring 46*o* provides resistance and pushes back on the second shock-pulsing mass 82*o*, returning the second shock-pulsing mass 82*o* to its original position and impacting against the impact surface 290 of the waveguide fitting 28*m*.

The movement of the second shock-pulsing mass 82*o* helps to amplify each shock pulse by reinforcing it with additional impact energy from the second shock-pulsing mass 82*o*. One having ordinary skill in the art will see that the position and effect of a the second shock-pulsing mass 82*o* will manipulate the shock pulses such that they may effectively change the axial displacement at the distal end of the ultrasonic waveguide 24*o*, which can be useful for different applications of the ultrasonic transducer.

Figure 29:
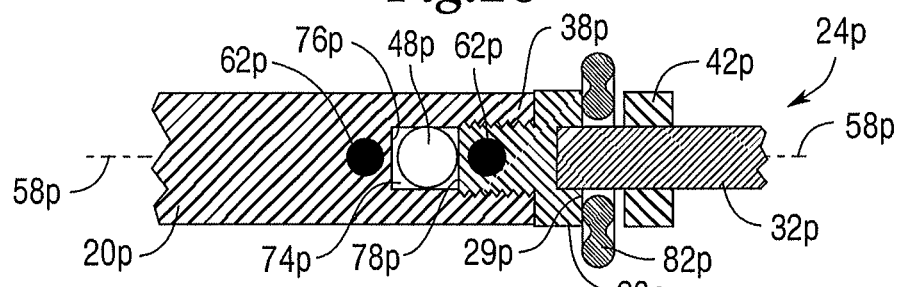
FIG. 29 shows a cross-section of the horn and ultrasonic waveguide on another embodiment of the ultrasonic transducer.

As shown in FIG. 29, in another embodiment of the ultrasonic transducer in which the horn 20*p* has a shock-pulsing mass 48*p* engaged within a centrally located cavity 74*p*, a second shock-pulsing mass 82*p* is positioned on the ultrasonic waveguide 24*p*. In this embodiment, the shock-pulsing mass 48*p* is a spherically shaped ball bearing, whereas, the second shock-pulsing mass 82*p* has a circular cross-section and double dog bone shape around the central axis 58*p*. It should be appreciated that the shock-pulsing mass 48*p* could have a shape other than spherical, so long as the shock-pulsing mass 48*p* can create shock-pulses while enclosed within the cavity 74*p*. Such shapes include, but are in no way limited to, a piston shape, an octagonal shape, or a cube shape, etc.

Here, the cavity 74*p* is calibrated to allow the shock-pulsing mass 48*p* to oscillate freely without the need of a spring pushing it against either the proximal end 76*p* of the cavity 74*p* or the proximal end 78*p* of the ultrasonic waveguide 24*p*. Axial displacement at the proximal end 76*p* of the cavity 74*p*, from the anti-node 62*p* position, impacts with the shock-pulsing mass 48*p*. The shock-pulsing mass 48*p* is then thrust forward, impacting with the proximal end 78*p* of the ultrasonic waveguide 24*p*. Axial displacement at the proximal end 78*p* of the ultrasonic waveguide 24*p*, from another anti-node 62*p* position, will subsequently impact the shock-pulsing mass and cause it to ricochet backwards and towards the proximal end 76*p* of the cavity 74*p*. These corresponding axial displacements create a back and forth movement of the shock-pulsing mass 48*p* between the proximal ends of both the cavity 74*p* and the ultrasonic waveguide 24*p*, creating a corresponding shock pulse along the ultrasonic waveguide 24*p*. One having ordinary skill in the art will see the length of the cavity 74*p* must be properly calibrated or the shock-pulsing mass 48*p* will not to move back and forth when the ultrasonic transducer (not shown) is held horizontally to the ground. One having ordinary skill in the art will also see that the frequency of ultrasonic vibrations will have to be modified so that the anti-node 62*p* positions will be located at their positions as shown.

The second shock-pulsing mass 82*p*, is non-fixedly engaged on the body of the ultrasonic waveguide 24*p*, in between the waveguide fitting 28*p* and stop 42*p*. The distance between the waveguide fitting 28*p* and stop 42*p* is calibrated to allow the second shock-pulsing mass 48*p* to oscillate freely without the need of a spring pushing it against either the waveguide fitting 28*p* or stop 42*p*. Shock pulses and ultrasonic vibrations emanating forward from the proximal end 78*p* of ultrasonic waveguide 24*p* will cause the second shock-pulsing mass 82*p* to thrust forward with each the shock pulse and impact with the stop 42*p*. After impacting with the stop 42*p*, the second shock-pulsing mass 82*p* will ricochet off the stop 42*p* and bounce back to its original position. The pattern of movement of the second shock-pulsing mass 82*p* causes it to move back and forth movement of between the waveguide fitting 28*p* and the stop 42*p*, facilitating the shock pulse created by the pattern of movement from the shock-pulsing mass 48*p*.

The movement of the second shock-pulsing mass 82p helps to amplify the shock pulse by reinforcing it with additional impact energy from the second shock-pulsing mass 82p impacting the stop 42p. One having ordinary skill in the art will see that the position and effect of a the second shock-pulsing mass 82p will manipulate the shock pulse such that it may effectively change the axial displacement at the distal end of the ultrasonic waveguide 24p, which can be useful for different applications of the ultrasonic transducer.

Figure 30:
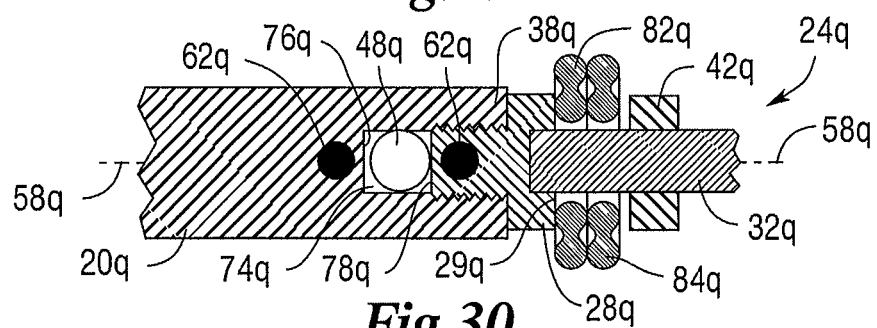
FIG. 30 shows a cross-section of the horn and ultrasonic waveguide on another embodiment of the ultrasonic transducer.

As shown in FIG. 30, in another embodiment of the ultrasonic transducer in which the horn 20q has a shock-pulsing mass 48q engaged within the centrally located cavity 74q, a second shock-pulsing mass 82q and third shock pulsing mass 84q are each positioned on the ultrasonic waveguide 24q. In this embodiment, the shock-pulsing mass 48q is a spherically shaped ball bearing, whereas, both the second shock-pulsing mass 82q and third shock-pulsing mass 84q have a circular cross-section and double dog bone shape around the central axis 58q. It should be appreciated that the shock-pulsing mass 48q could have a shape other than a spherical, so long as the shock-pulsing mass 48q can create shock-pulses while enclosed within the cavity 74q. Such shapes include, but are in no way limited to, a piston shape, an octagonal shape, or a cube shape, etc.

Here, the cavity 74q is calibrated to allow the shock-pulsing mass 48q to oscillate freely without the need of a spring pushing it against either the proximal end 76q of the cavity 74q or the proximal end 78q of the ultrasonic waveguide 24q. Axial displacement at the proximal end 76q of the cavity 74q, from the anti-node 62q position, impacts with the shock-pulsing mass 48q. The shock-pulsing mass 48q is then thrust forward, impacting with the proximal end 78q of the ultrasonic waveguide 24q. Axial displacement at the proximal end 78q of the ultrasonic waveguide 24q, from another anti-node 62q position, will subsequently impact the shock-pulsing mass 48q and cause it to ricochet backwards and towards the proximal end 76q of the cavity 74q. These corresponding axial displacements create a back and forth movement of the shock-pulsing mass 48q between the proximal ends of both the cavity 74q and the ultrasonic waveguide 24q, creating a corresponding shock pulse along the ultrasonic waveguide 24q. One having ordinary skill in the art will see the length of the cavity 74q must be properly calibrated or the shock-pulsing mass 48q will not move back and forth when the ultrasonic transducer (not shown) is held horizontally to the ground. One having ordinary skill in the art will also see that the frequency of ultrasonic vibrations will have to be modified so that the anti-node 62q positions will be located at their positions as shown.

Both the second shock-pulsing mass 82q and third shock-pulsing mass 84q are non-fixedly engaged on the body of the ultrasonic waveguide 24q, in between the waveguide fitting 28q and stop 42q. The distance between the waveguide fitting 28q and stop 42q is calibrated to allow both the second shock-pulsing mass 82q and third shock-pulsing mass 84q to oscillate freely without the need of a spring pushing either against the waveguide fitting 28q or stop 42q. Shock pulses and ultrasonic vibrations emanating forward from the proximal end 78q of ultrasonic waveguide 24q will cause the second shock-pulsing mass 82q to thrust forward with each the shock pulse and impact with the third shock pulsing mass 84q, which will then impact with the stop 42q. After impacting with the stop 42q, the third shock-pulsing mass 82q will ricochet off the stop 42q and impact with the second shock-pulsing mass 82q, sending both back to their original positions. The pattern of movement of both the second shock-pulsing mass 82q and the third shock-pulsing mass 84q causes each to move back and forth between the waveguide fitting 28q and the stop 42q. This pattern of movement also facilitates the shock pulse created by the other pattern of movement from the shock-pulsing mass 42q.

The movement of the second shock-pulsing mass 82q and third shock pulsing mass 84q helps to amplify the shock pulse by reinforcing it with additional impact energy from the third shock-pulsing mass 84q impacting with the stop 42q. One having ordinary skill in the art will see that the position and effect of both the second shock-pulsing mass 82q and the third shock-pulsing mass 82q will manipulate the shock pulse such that it may effectively change the axial displacement at the distal end of the ultrasonic waveguide 24q, which can be useful for different applications of the ultrasonic transducer.

Figure 31:
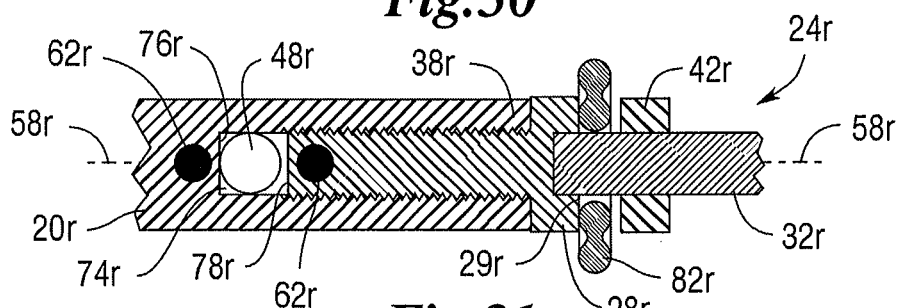
FIG. 31 shows a cross-section of the horn and ultrasonic waveguide on another embodiment of the ultrasonic transducer.

As shown in FIG. 31, the embodiment of the ultrasonic transducer functions in substantially the same way as the embodiment shown in FIG. 28 above. However, in this embodiment the proximal end 78r of the ultrasonic waveguide 24r extends much deeper into the horn 20r than in any of the embodiments discussed above. The shock-pulsing mass 48r is a spherically ball bearing, whereas, the second shock-pulsing mass 82r has a circular cross-section and double dog bone shape around the central axis 58r. It should be appreciated that the shock-pulsing mass 48r could have a shape other than a spherical, so long as the shock-pulsing mass 48r can create shock-pulses while enclosed within the cavity 74r. Such shapes include, but are in no way limited to, a piston shape, an octagonal shape, or a cube shape, etc.

Here, the cavity 74r is calibrated to allow the shock-pulsing mass 48r to oscillate freely without the need of a spring pushing it against either the proximal end 76r of the cavity 74r or the proximal end 78r of the ultrasonic waveguide 24r. Axial displacement at the proximal end 76r of the cavity 74r, from the anti-node 62r position, impacts with the shock-pulsing mass 48r. The shock-pulsing mass 48r is then thrust forward, impacting with the proximal end 78r of the ultrasonic waveguide 24r. Axial displacement at the proximal end 78r of the ultrasonic waveguide 24r, from another anti-node 62r position, will subsequently impact the shock-pulsing mass and cause it to ricochet backwards and towards the proximal end 76r of the cavity 74r. These corresponding axial displacements create a consistent and equal back and forth movement of the shock-pulsing mass 48r between the proximal ends of both the cavity 74r and the ultrasonic waveguide 24r, creating a corresponding shock pulse along the ultrasonic waveguide 24r. One having ordinary skill in the art will see the length of the cavity 74r must be properly calibrated or the shock-pulsing mass 48r will not to move back and forth when the ultrasonic transducer (not shown) is held horizontally to the ground. One having ordinary skill in the art will also see that the frequency of ultrasonic vibrations will have to be modified so that the anti-node 62r positions will be located at their positions as shown.

The second shock-pulsing mass 82r, is non-fixedly engaged on the body of the ultrasonic waveguide 24r, in between the waveguide fitting 28r and stop 42r. The distance between the waveguide fitting 28r and stop 42r is calibrated to allow the second shock-pulsing mass 48r to oscillate freely without the need of a spring pushing it against either the waveguide fitting 28r or stop 42r. Shock pulses and ultrasonic vibrations emanating forward from the proximal end 78r of ultrasonic waveguide 24r will cause the second shock-pulsing mass 82r to thrust forward with each the shock pulse and impact with the stop 42r. After impacting with the stop 42r, the second shock-pulsing mass 82r will ricochet off the stop 42r and bounce back to its original position. The pattern of movement of the second shock-pulsing mass 82r causes it to move back and forth between the waveguide fitting 28r and the stop 42r, facilitating the shock pulse created by the pattern of movement from the shock-pulsing mass 42r.

The movement of the second shock-pulsing mass 82r helps to amplify the shock pulse by reinforcing it with additional impact energy from the second shock-pulsing mass 82r impacting the stop 42r. One having ordinary skill in the art will see that the position and effect of a the second shock-pulsing mass 82r will manipulate the shock pulse such that it may effectively change the axial displacement at the distal end of the ultrasonic waveguide 24r, which can be useful for different applications of the ultrasonic transducer.

Figure 32:
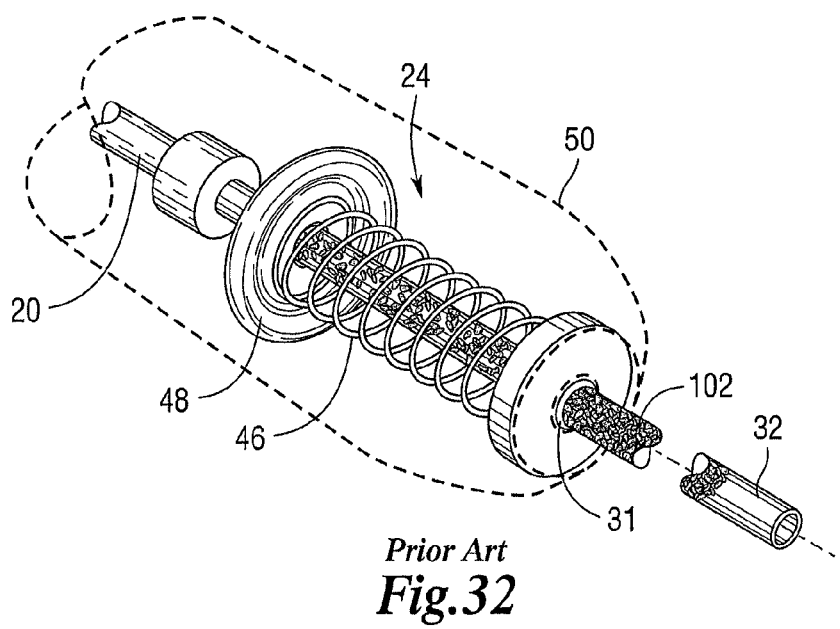
FIG. 32 shows a perspective view of a prior art ultrasonic waveguide having wear debris manifested on its body.
Figure 33:
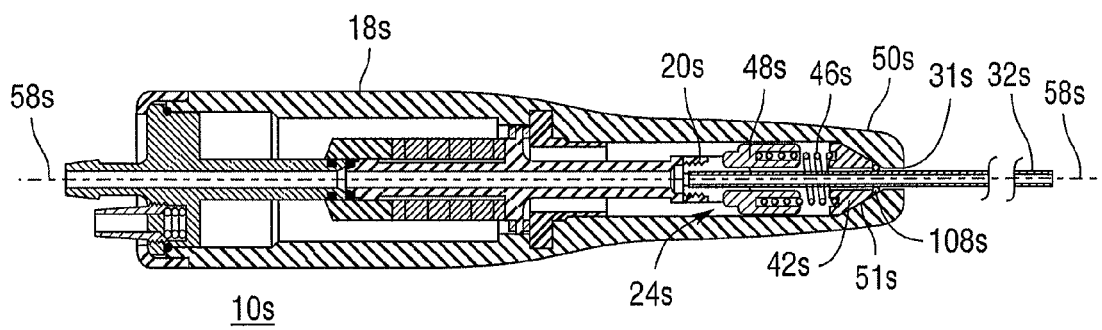
FIG. 33 shows a cross-section of another embodiment of the ultrasonic transducer.
Figure 34:
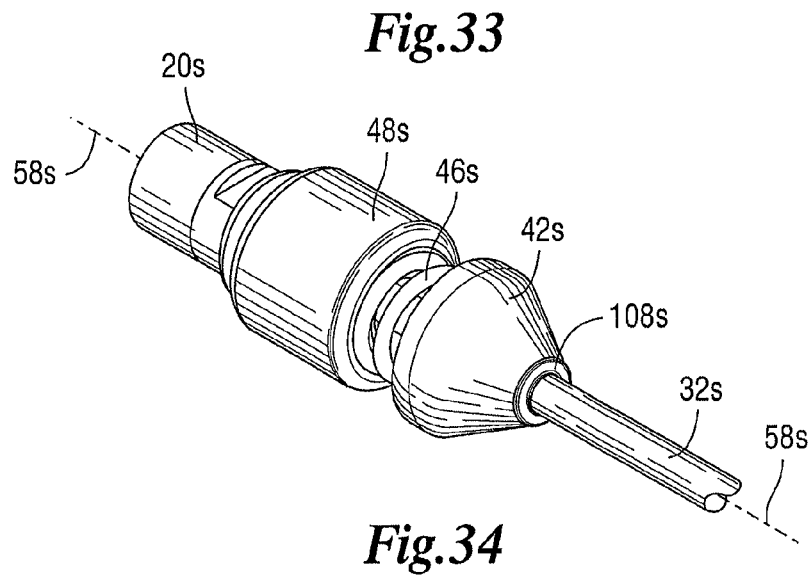
FIG. 34 shows a perspective view of the ultrasonic waveguide of the ultrasonic transducer of FIG. 34.

As can be seen in FIG. 32, extended use of the ultrasonic transducer causes wear debris 102, mixed with fluid, to slowly flow through the opening 31 at the tip of the nosecone 50 and manifest itself on the waveguide tube 32 of the ultrasonic waveguide 24. This manifestation causes concern with users of the ultrasonic transducer, as it is perceived as a sanitary issue for surgical procedures. Furthermore, when an ultrasonic transducer is used in an upward orientation, fluid from surgical procedures can easily find its way into the opening 31. This unwanted fluid is problematic for surgeries because it creates viscous resistance that dampens the vibrational energy caused by the waveguide's shock-pulsing mass 48. Loss of vibrational energy creates efficiency issues for surgeons while they are depending on the waveguide tube 32 to vibrate at certain amplitudes during their surgeries. The unwanted fluid is also problematic because it may cause rust to form on the components of the ultrasonic waveguide.

The embodiments shown in FIGS. 33 through 37, are presented to address problems associated with the wear debris and unwanted fluid. In this embodiment, a nose cone having a conical inner surface 51s is located next to the opening 31s of the nose cone 50s. The ultrasonic waveguide 24s has a corresponding conical shaped stop 42s with a tapered conical side 104s and a flat back side 106s. The conical shape of the stop 42s allows it to fit between the tip of the inner surface 51s of the nose cone 50s and the spring 46s, so that the conical side 104s of the stop 42s presses up against the tip of the inner surface 51s. The orientation of the stop 42s and inner surface 51s allows the two components to interlock with each other. As further discussed below, pressure from both the spring 46s and shock-pulsing mass 42s presses the conical side 104s of the stop 42s against the nose cone 50s and ensures the two components remain interlocked with each other.

A sealing implement 108s, which is an elastomeric o-ring in this embodiment, is disposed between the inner surface 51s of the nose cone 50s and the conical side 104s of the stop 42s. Working in conjunction with each other, the stop 42s and sealing implement 108s form a seal that closes off the opening 31s when the stop 42s is pressed up against the inner surface 51s of the nosecone 50s. This seal keeps wear debris from flowing out through the opening 31s and manifesting itself along the waveguide tube 32s. This seal also prevents unwanted fluids from being able to get inside the nosecone 50s and causing the associated damping problems or rusting problems or both. It will be appreciated that the sealing implement 108s may be something other than an o-ring or may be made from something other than elastomeric material. Any sealing implement 108s that forms a proper seal is acceptable.

Figure 35:
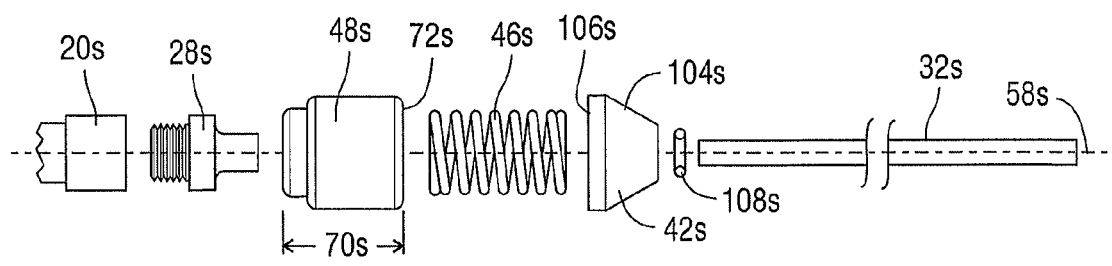
FIG. 35 shows an exploded side view of the ultrasonic waveguide of the ultrasonic transducer of FIG. 34.
Figure 36:
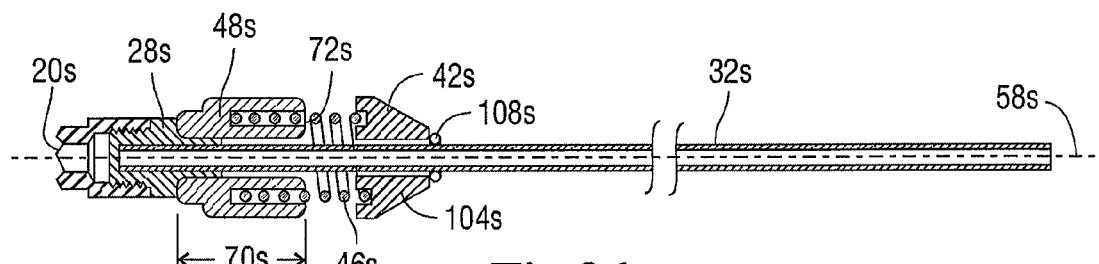
FIG. 36 shows a cross-section of the ultrasonic waveguide of FIG. 34.
Figure 37:
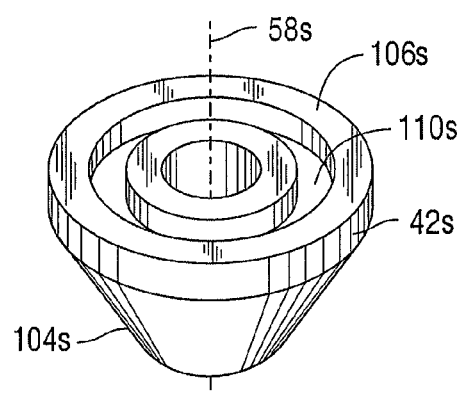
FIG. 37 shows a perspective view of the backside of the stop of the ultrasonic waveguide of FIG. 34.

Referring to FIGS. 35 through 37, the back side 106s of the stop 42s has a round indentation 110s facilitating the interlocking of both the spring 46s and stop 42s when the spring 46s presses against the stop 42s. The embodiment in which the shock-pulsing mass 48s has a circular cross-section 66s and a tubular length 70s around the central axis 58s is ideal for this embodiment of the ultrasonic waveguide (as shown in FIGS. 18A through 18C). This is because round trench 72s cut into the tubular length 70s of the shock-pulsing mass 48s, comparable to the connection of the back side 106s of the stop 42s, interlocks with the spring 46s and creates stability for the spring 46s as it interlocks with the stop 42s. It will be understood that the trench 72s could be any shape that is cut to fit the corresponding shock-pulsing mass 48s.

This invention has been described with reference to several preferred embodiments. Many modifications and alterations will occur to others upon reading and understanding the preceding specification. It is intended that the invention be construed as including all such alterations and modifications in so far as they come within the scope of the appended claims or the equivalents of these claims.

The invention claimed is:

1. A device for the transmission of ultrasonic vibrations that establishes a plurality of node and anti-node positions along a central axis of an ultrasonic waveguide, said device comprising: said ultrasonic waveguide comprising: a waveguide tube, a waveguide fitting, and an impact surface; said waveguide tube having a proximal end and a distal end; said waveguide fitting having an attachment end and a waveguide tube coupler; said waveguide tube coupler adapted to receive and fixedly secure to said proximal end of said waveguide tube; a spring and a shock-pulsing mass, each positioned on said ultrasonic waveguide; a stop positioned on said ultrasonic waveguide; said spring and said shock-pulsing mass are both interposed between said stop and said impact surface; a second shock-pulsing mass; said second shock-pulsing mass abuts against said stop; said shock-pulsing mass abuts against said impact surface; and said spring positioned between said shock-pulsing mass and said second shock-pulsing mass; and said impact surface positioned within at least one $\lambda/6$ of an anti-node position along the central axis of said ultrasonic waveguide when said attachment end of said waveguide fitting is attached to an operating device.

2. The device of claim 1 wherein said stop is positioned within at least one $\lambda/6$ of an anti-node position along the central axis of said ultrasonic waveguide.

3. The device of claim 1 wherein said stop is positioned within at least one $\lambda/3$ of an anti-node position along the central axis of said ultrasonic waveguide.

4. The device of claim 1 wherein said stop is positioned on an anti-node position along the central axis of said ultrasonic waveguide.

5. The device of claim 1 wherein each of said spring, said shock-pulsing mass, and said stop are positioned on said waveguide fitting.

6. The device of claim 1 wherein each of said spring, said shock-pulsing mass, and said stop are positioned on said waveguide tube.

7. The device of claim 1 wherein said shock-pulsing mass has a circular cross-section and a double dog bone shape around the central axis.

8. The device of claim 1 wherein said shock-pulsing mass has a circular cross-section and a donut shape around the central axis.

9. The device of claim 1 wherein said shock-pulsing mass having a circular cross-section and a tubular length, said tubular length having a trench.

10. The device of claim 1 further comprising:
a sealing implement positioned on said ultrasonic waveguide; and
said stop and said sealing implement working in conjunction to create a seal when said ultrasonic waveguide is installed within an operating device.

11. A device for the transmission of ultrasonic vibrations that establishes a plurality of node and anti-node positions along a central axis of an ultrasonic waveguide, said device comprising: said ultrasonic waveguide comprising: a waveguide tube, a waveguide fitting, and an impact surface; said waveguide tube having a proximal end and a distal end; said waveguide fitting having an attachment end and a waveguide tube coupler; said waveguide tube coupler adapted to receive and fixedly secure to said proximal end of said waveguide tube; a spring and a shock-pulsing mass, each positioned on said ultrasonic waveguide; a stop positioned on said ultrasonic waveguide; said spring and said shock-pulsing mass are both interposed between said stop and said impact surface; a second shock-pulsing mass; said second shock-pulsing mass abuts against said stop; said shock-pulsing mass abuts against said impact surface; and said spring positioned between said shock-pulsing mass and said second shock-pulsing mass; an adjustment means for adjusting the position of said stop along the central axis of said ultrasonic waveguide; and said impact surface positioned within at least one $\lambda/6$ of an anti-node position along the central axis of said ultrasonic waveguide when said attachment end of said waveguide fitting is attached to an operating device.

12. The device of claim 11 wherein each of said spring, said shock-pulsing mass, and said stop are positioned on said waveguide fitting.

13. The device of claim 11 wherein each of said spring, said shock-pulsing mass, and said stop are positioned on said waveguide tube.

14. The device of claim 11 wherein said shock-pulsing mass has a circular cross-section and a double dog bone shape around the central axis.

15. The device of claim 11 wherein said shock-pulsing mass has a circular cross-section and a donut shape around the central axis.

16. The device of claim 11 wherein said shock-pulsing mass having a circular cross-section and a tubular length, said tubular length having a trench.

\* \* \* \* \*